(12) United States Patent
Roth

(10) Patent No.: US 8,250,021 B2
(45) Date of Patent: Aug. 21, 2012

(54) METHODS, STORAGE MEDIUMS, AND SYSTEMS FOR CONFIGURING CLASSIFICATION REGIONS WITHIN A CLASSIFICATION MATRIX OF AN ANALYSIS SYSTEM AND FOR CLASSIFYING PARTICLES OF AN ASSAY

(75) Inventor: Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 621 days.

(21) Appl. No.: 12/505,224

(22) Filed: Jul. 17, 2009

(65) Prior Publication Data

US 2010/0017358 A1    Jan. 21, 2010

Related U.S. Application Data

(60) Provisional application No. 61/081,558, filed on Jul. 17, 2008.

(51) Int. Cl.
*G06F 17/00* (2006.01)
*G06N 7/04* (2006.01)

(52) U.S. Cl. ........................................................ 706/54

(58) Field of Classification Search .................. None
See application file for complete search history.

(56) References Cited

U.S. PATENT DOCUMENTS

| | | | |
|---|---|---|---|
| 4,959,798 A * | 9/1990 | Gordon et al. | 701/28 |
| 5,981,180 A | 11/1999 | Chandler et al. | |
| 6,524,793 B1 | 2/2003 | Chandler et al. | |
| 6,939,720 B2 | 9/2005 | Chandler et al. | |
| 7,551,763 B2 | 6/2009 | Calvin et al. | |
| 2002/0052690 A1 | 5/2002 | Nivlet et al. | |
| 2005/0073686 A1 * | 4/2005 | Roth et al. | 356/436 |
| 2005/0164261 A1 | 7/2005 | Chandler et al. | |
| 2005/0202469 A1 | 9/2005 | Chandler et al. | |
| 2005/0251347 A1 | 11/2005 | Perona et al. | |

FOREIGN PATENT DOCUMENTS

| | | |
|---|---|---|
| WO | 2005/071389 | 8/2005 |
| WO | 2007/016517 | 2/2007 |
| WO | 2008/098284 | 8/2008 |

OTHER PUBLICATIONS

JPEG http://en.wikipedia.org/wiki/Jpeg, 2008.*
International Search Report & Written Opinion, PCT/US2009/051039, mailed Jan. 29, 2010.
U.S. Appl. No. 11/461,582, filed Aug. 1, 2006.

* cited by examiner

*Primary Examiner* — Alan Chen
*Assistant Examiner* — Li-Wu Chang
(74) *Attorney, Agent, or Firm* — Fulbright & Jaworski L.L.P.

(57) ABSTRACT

Methods and systems are provided which include configurations for the reassigning unit locations of a classification matrix at which two or more classification regions overlap as non-classification regions. In addition, methods and systems are provided which include configurations for mathematically creating classification regions which may be characterized by values which more accurately correspond to measured values of particles. Other embodiments of methods and systems include configurations for acquiring data corresponding to measurable parameters of a particle and identifying a location within a classification matrix to which at least some of the data corresponds. Such methods and systems further include configurations for translating either the data corresponding to the identified unit location or a target space located at known locations within the classification matrix a preset number of predetermined coordinate paths until a conclusion that the particle may be classified to particular particle category or a reject class is attained.

27 Claims, 7 Drawing Sheets

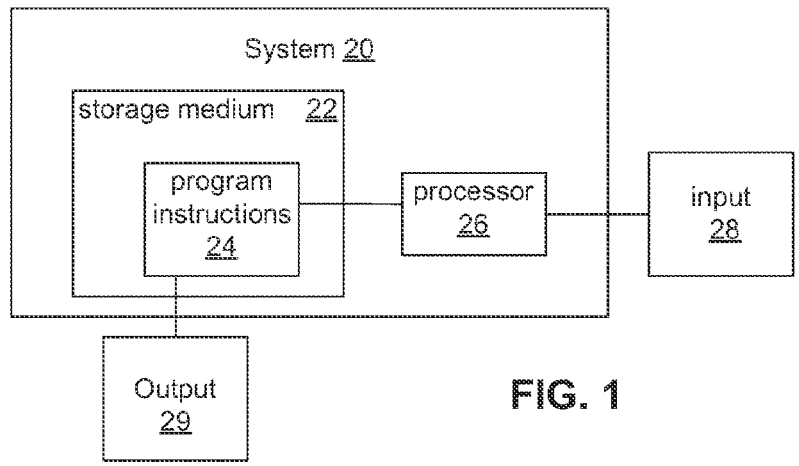
FIG. 1
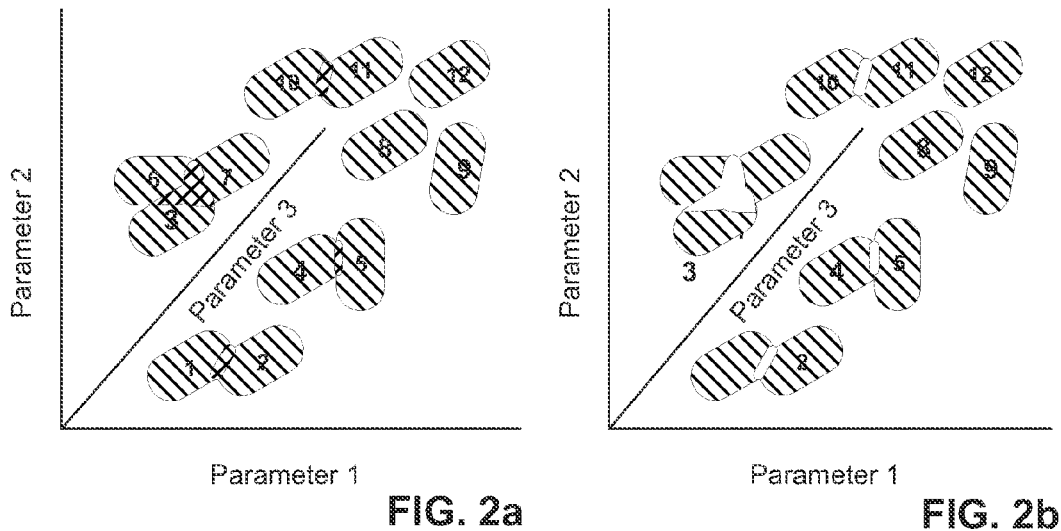
FIG. 2a
FIG. 2b
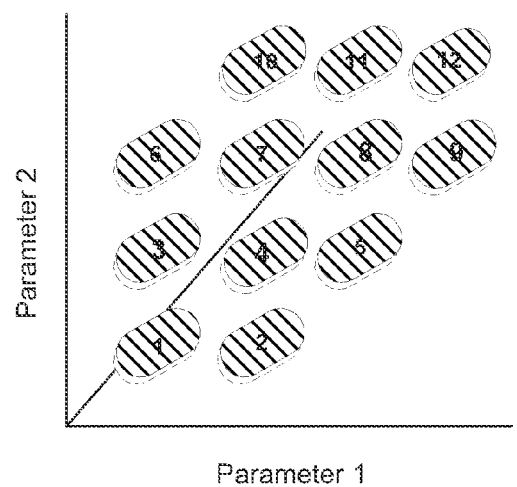
FIG. 3

METHODS, STORAGE MEDIUMS, AND SYSTEMS FOR CONFIGURING CLASSIFICATION REGIONS WITHIN A CLASSIFICATION MATRIX OF AN ANALYSIS SYSTEM AND FOR CLASSIFYING PARTICLES OF AN ASSAY

BACKGROUND OF THE INVENTION

1 Field of the Invention

This invention generally relates to methods, storage mediums, and systems for configuring classification regions within a classification matrix of an assay analysis system and further relates to methods, storage mediums, and systems for classifying particles of an assay.

2. Description of the Related Art

The following descriptions and examples are not admitted to be prior art by virtue of their inclusion within this section.

Spectroscopic techniques are widely employed in the analysis of chemical and biological assays. Most often, these techniques involve measuring the absorption or emission of electromagnetic radiation by the material of interest. One such application is in the field of microarrays, which is a technology exploited by a large number of disciplines including the combinatorial chemistry and biological assay industries. Luminex Corporation of Austin, Tex. has developed systems in which biological assays are analyzed through detection of fluorescence emissions from the surface of variously colored fluorescent particles. The systems may also analyze an assay via measurements of the level of light scattered by a particle, the electrical impedance of a particle, as well as other parameters.

In some cases, a multiplexing scheme is employed in assay analysis systems such that multiple analytes may be evaluated in a single analysis process for a single sample. To facilitate a multiplexing scheme, particles are configured into distinguishable groups, with different groups used to indicate the presence, absence, and/or amount of different analytes in an assay. For instance, different fluorescent dyes and/or different concentrations of dyes may be absorbed into particles and/or bound to the surface of particles and/or particles may vary by size. Conventional systems using these categorical particles can test for tens to over one hundred different analytes in an assay using a two-dimensional classification matrix. Although the number of particle categories (and thus the number of analytes to be detected) may be augmented by increasing the number of dyes and/or different dye intensities, an augmentation of particle category quantity generally necessitates an increase in the size of a classification matrix. As set forth below, the size of a classification matrix and available space within a classification matrix for positioning classification regions may be finite and, thus, efficient distribution of classifications regions is needed and becomes more challenging as the number of classification regions is increased.

In assay analysis systems which utilize fluorescence emissions to classify particles, the range of fluorescent values is generally limited by the minimum amount of dye that is detectable by avalanche photo diodes and further by the maximum amount of dye that can be retained by the particles. In view thereof, classification matrices associated with such systems are sometimes framed by more than two parameters to increase the available classification space, specifically in cases in which more than 100 particle categories exist for an assay. Classification matrices framed by more than two parameters, however, may be particularly prone to restrictions of available space. More specifically, detection channels of fluorescence emissions are generally not orthogonal and, thus, there may be crosstalk among channels (i.e., an increase and/or an addition of one dye may affect one or more of the other channels to some degree). Consequently, there may be areas of a classification matrix which may not be suitable for classification regions (i.e., areas which are affected by crosstalk). Such a restriction of available space may be particularly germane in classification matrices framed by more than two parameters due to the increase and/or addition of dyes to facilitate such matrices relative to two-dimensional classification matrices.

Regardless of the number of parameters framing a classification matrix, one manner in which to fit classification regions within a classification matrix and insure distinct categorization is to configure small and widely spaced classification regions. However, such a tactic often results in poor classification efficiency since the percentage of particles fitting into the small and widely spaced classification regions will be relatively low. Higher classification efficiencies impart more precise analysis results and, thus, it is generally advantageous to configure a classification region to encompass a majority of possible measurement values for a subset of particles, and more specifically, greater than approximately 90% of possible measurement values for a subset of particles. Such high classification efficiencies, however, are generally difficult to attain, particularly in cases in which more than 100 particle categories exist for an assay since configurations (i.e., size, shape, and angle) of different classification regions tend to vary more as the number of particle categories increase and, in some embodiments, may overlap. Overlapping classification regions are particularly undesirable due to the potential of misclassifying a particle to more than one classification region and, thus, are generally avoided. As a result, classification regions are generally reduced to the next smaller size according to the scale of the units framing the classification matrix, significantly limiting the size of the regions and impairing the ability to attain high classification efficiencies.

A further challenge for assay analysis systems is the extensive memory capacity required to store the configuration parameters for classification regions. In particular, given a particular level of scale granularity by which a classification matrix is framed, additional memory capacity is generally needed to store additional classification regions. Furthermore, the more parameters used to define classification regions, the more memory capacity needed. In some cases, limitations of system memory capacity may prohibit the number of classification regions that may be considered for assays and, thus, undesirably limit the breadth of a multiplexing scheme. In some embodiments, classification matrices are framed by scales of less granularity than the scales of values which may be measured from particles, specifically to reduce system memory capacity. For example, in some embodiments, classification matrices may be framed by scales of integers computed from logarithmic values of measured parameters of particles. In such cases, however, converting measured values of particles to fit the logarithm scale of a classification matrix may skew the values, reducing the accuracy of particle classification. Furthermore, systems employing such classification matrices may still have memory capacity limitations prohibiting the number of classification regions that may be considered for assays.

Accordingly, it would be desirable to develop methods and systems for configuring classification regions which are efficiently distributed within a classification matrix and result in sufficiently high classification efficiencies. Furthermore, it would be beneficial to develop a method for creating classification regions which may be characterized by values which more accurately correspond to measured values of particles. Moreover, it would be advantageous to develop methods and systems for classifying particles to a plurality of classification regions without severely increasing memory usage of a system.

SUMMARY OF THE INVENTION

The following description of various embodiments of methods, storage mediums, and systems for configuring classification regions within a classification matrix of an assay analysis system and various embodiments of methods, storage mediums, and systems for classifying particles of an assay is not to be construed in any way as limiting the subject matter of the appended claims.

Embodiments of the methods, storage mediums, and systems include configurations for identifying a plurality of classification regions within a classification matrix which is framed by ranges of values associated with one or more measurable parameters of particles that are configured for assay analysis. In addition, the methods, storage mediums, and systems include configurations for the reassigning unit locations jointly assigned to two or more of the plurality of classification regions as non-classification regions.

Other embodiments of the methods, storage mediums, and systems include configurations for mathematically transforming a first value that corresponds to a point within an assay particle population category into a second value and converting the second value to a first integer. The methods, storage mediums, and systems further include configurations for mathematically transforming the first integer into a third value, converting the third value to a second integer, and designating the second integer as a replacement value for the point within the assay particle population category.

Other embodiments of the methods, storage mediums, and systems include configurations for acquiring data corresponding to measurable parameters of a particle and identifying a unit location within a classification matrix to which at least some of the data for an individual particle corresponds. The methods, storage mediums, and systems further include configurations for translating either the data corresponding to the identified unit location or a target space located at known locations within the classification matrix a preset number of predetermined coordinate paths until a conclusion that the particle may be classified to particle population or a reject class is attained. In some cases, the methods, storage mediums, and systems are configured to iterate such steps through a plurality of target spaces until the particle is classified.

BRIEF DESCRIPTION OF THE DRAWINGS

Other objects and advantages of the invention will become apparent upon reading the following detailed description and upon reference to the accompanying drawings in which:

FIG. 1 illustrates a schematic diagram of a system including a storage medium having program instructions configured to perform the processes described in reference to FIGS. 2a-12;

FIGS. 2a and 2b illustrate graphical representations of exemplary classification matrices and classification regions used for describing the processes outlined in FIG. 4;

FIG. 3 illustrates a graphical representation of an exemplary classification matrix and an exemplary shift of classification regions resulting from processes outlined in FIG. 5;

Figure 4:
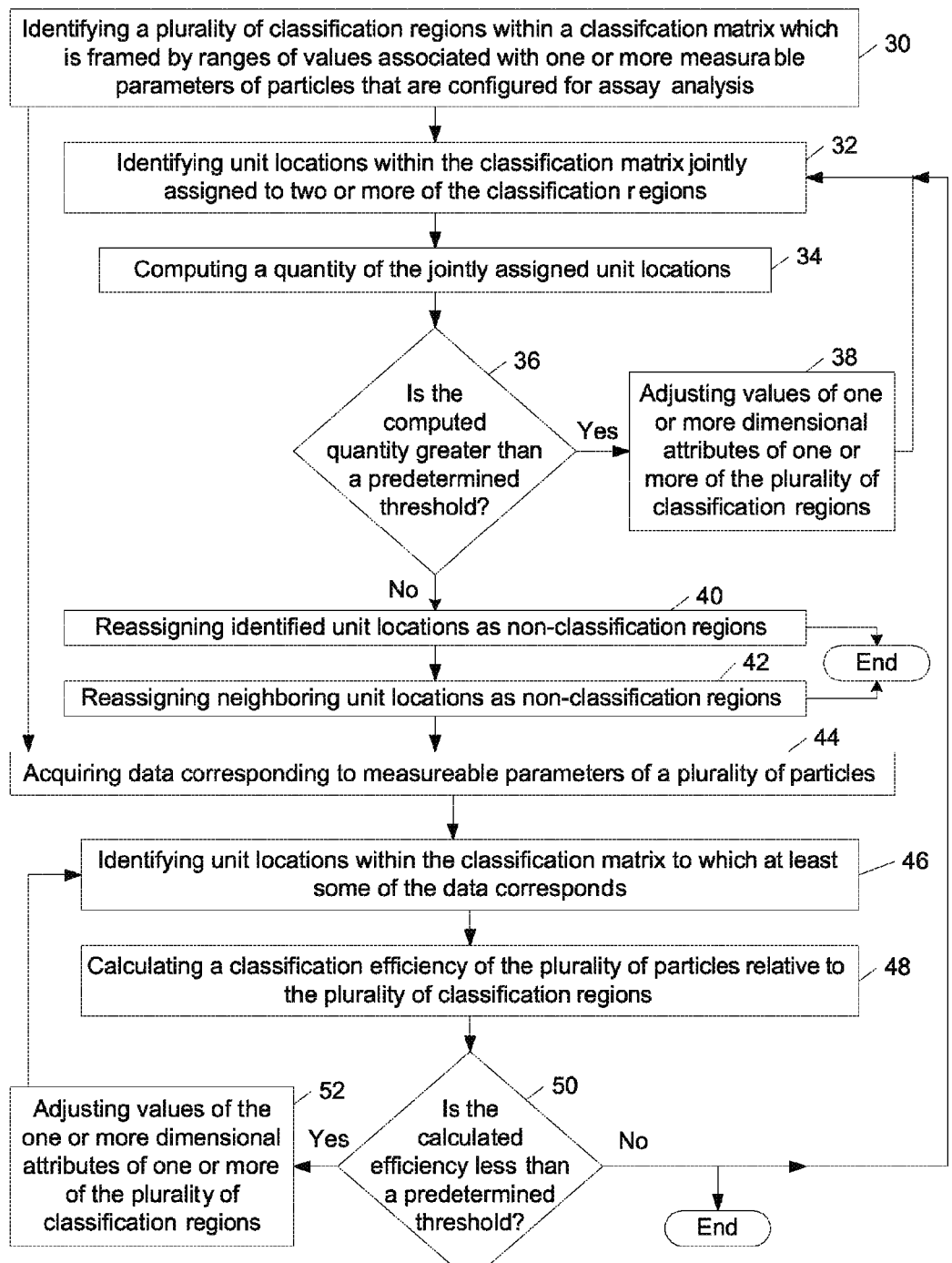
FIGS. 4 and 5 illustrate flowcharts of exemplary methods for configuring classification regions within a classification matrix of an assay analysis system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 5:
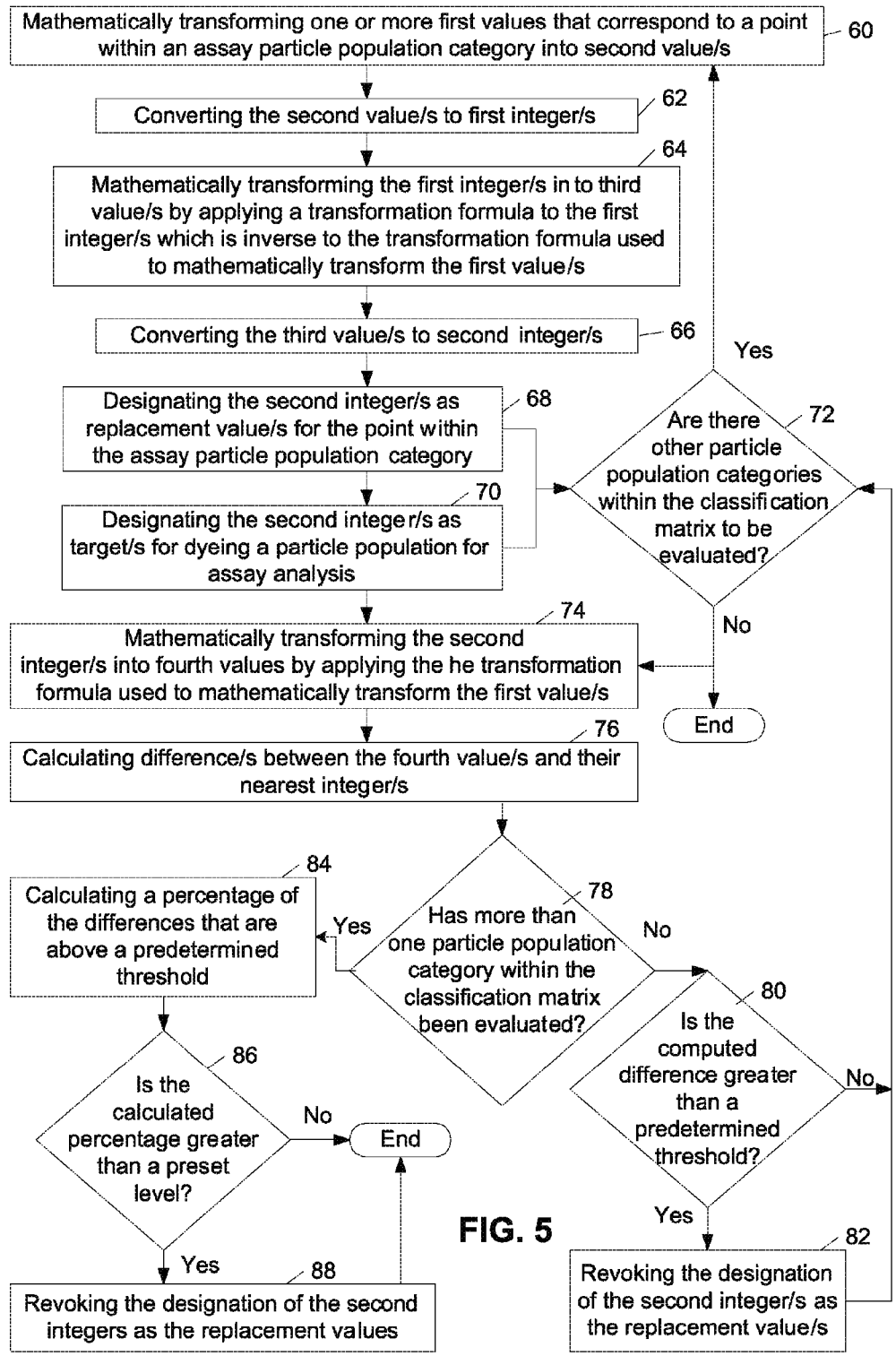

Turning to the drawings, exemplary methods, storage mediums, and systems for configuring classification regions within a classification matrix of an assay analysis system are provided. In addition, exemplary methods, storage mediums, and systems for classifying particles of an assay are provided. In particular, FIGS. 4 and 5 depict flowcharts for configuring classification regions within a classification matrix of an assay analysis system. FIGS. 6, 7, 11, and 12, on the other hand, depict flowcharts for classifying particles of an assay. An exemplary system is depicted in FIG. 1 having a storage medium which includes program instructions configured to perform the processes outlined in the flowcharts depicted in FIGS. 4-7, 11, and 12. FIGS. 2a-3 and 8-10 illustrate graphical representations of classification matrices and/or target spaces for describing the processes outlined in the flowcharts.

It is noted that the methods, storage mediums, and systems described herein are not necessarily dependent upon the classification matrices and classification regions being graphically depicted in a physical sense. Rather, the classification matrices and classification regions described herein may have, in a sense, a virtual existence. FIGS. 2a-3 and 8-10 are primarily used to help explain the intricacies of the methods, program instructions, and systems described herein. It is noted that the systems, storage mediums, and methods described herein may, in some cases, be configured to perform processes other than those associated with configuring classification regions and/or classifying particles and, therefore, the systems, storage mediums, and methods described herein are not necessarily limited to the depictions of FIGS. 1-12.

As shown in FIG. 1, system 20 includes storage medium 22 and processor 26. System 20 may take various forms, including a personal computer system, mainframe computer system, workstation, network appliance, Internet appliance, personal digital assistant (PDA), a digital signal processor (DSP), field programmable gate array (FPGA), or other device. In any case, storage medium 22 includes program instructions 24 which are executable using processor 26 for generating and transmitting output 29, particularly performing the processes outlined below in reference to FIGS. 4-7, 11, and 12. In some cases, system 20 may be configured to receive input 28 to activate program instructions 24 though processor 26 and/or contribute data for program instructions 24 to process. In addition or alternatively, storage medium 22 may include databases and/or look-up tables which the program instructions may access for performing the processes outlined below in reference to FIGS. 4-7, 11, and 12. Exemplary databases and/or look-up tables that may be included in storage medium 22 are described in reference to FIGS. 8-10.

In general, the term "storage medium," as used herein, may refer to any electronic medium configured to hold one or more set of program instructions, such as but not limited to a read-only memory, a random access memory, a magnetic or optical disk, or magnetic tape. The term "program instructions" may generally refer to commands within a program which are configured to perform a particular function, such as configuring classification regions within a classification matrix of an assay analysis system or classifying particles of an assay as described in more detail below. Program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Systems that may be configured to perform one or more of the processes described herein (i.e., systems which may include or be connected to system 20) include, but are not limited to, the Luminex® 100™, the Luminex® HTS, the Luminex® 100E, Luminex® 200™, and any further add-ons to this family of products that are available from Luminex Corporation of Austin, Tex. It is to be understood, however, that the methods, storage mediums, and systems described herein may use or may be configured to use particle data acquired by any assay measurement system. Examples of measurement systems include flow cytometers and static fluorescent imaging systems. In addition, although various parameters are described herein that can be used for particle classification, it is to be understood that the embodiments described herein may use any measurable parameter of particles that can be used to distinguish different populations of the particles and, thus, should not necessarily be limited to fluorescent properties of particles. Furthermore, the methods, storage mediums, and systems described herein may be applied to systems for analyzing any type of assay, specifically any biological, chemical, or environmental assay in which determination of the presence or absence of one or more analytes of interest is desired.

As noted above, program instructions 24 may be generally configured to perform the processes outlined in the flowcharts depicted in FIGS. 4-7, 11, and 12. As such, the flowcharts depicted in FIGS. 4-7, 11, and 12 generally describe methods carried out through the use of a software module. More specifically, the methods described in reference to FIGS. 4-7, 11, and 12 include analyzing and computing a relatively large amount of data through the use of one or more algorithms and, therefore, may be best implemented through a computer. Consequently, the methods described in reference to FIGS. 4-7, 11, and 12 may be referred to as "computer-implemented methods".

As used herein, the term "classifying" is generally referred to as categorizing particles of an assay into population groups in which member particles have similar properties. The population groups are referred to herein as "particle populations." In some cases, the term "assay particle population" may be used herein to specifically reference a particle population configured for assay analysis. Classification is of particular importance since often a sample will be analyzed with multiple, different populations of particles in a single experiment of an assay (i.e., in a multiplexing scheme). In particular, different populations of particles typically have at least one different characteristic such as the type of substance coupled to the particles and/or the quantity of substance(s) coupled to the particles such that the presence of different types and/or quantities of analytes within the sample can be detected and/or quantified in a single pass through an assay analysis system. To interpret the measurement results, the identity or classification of individual particles in the assay may be determined such that the measurement values may be correlated to the properties of the individual particles. In this manner, the measurement values associated with the different populations of particles can be distinguished and respectively attributed to the analytes of interest. In order to classify particles of an assay, the measurement values may be correlated to a classification matrix, which as described in more detail below is referred to herein as an array of values (actual or virtual) corresponding to measured parameters of particles used for classification. A plurality of classification regions may be defined in the classification matrix for categorizing the particles and, thus, the term "classification region" as used herein refers to an area of a classification matrix to which a population of particles may be classified.

The term "particle" is used herein to generally refer to microparticles, microspheres, polystyrene beads, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substrates or substances known in the art. Any of such terms may be used interchangeably herein. The methods, storage mediums, and systems described herein may be used for classification of any type of particles. In some cases, the methods, storage mediums, and systems described herein may be particularly used for particles serving as vehicles for molecular reactions. Exemplary molecular reaction particles which are used in flow cytometry include xMAP® microspheres, which may be obtained commercially from Luminex Corporation of Austin, Tex.

A flowchart of an exemplary method for configuring particle classification regions for an assay analysis system is depicted in FIG. 4. FIGS. 2a and 2b illustrate graphical representations of classification matrices and classification regions resulting from the processes outlined in FIG. 4 and, thus, are discussed in conjunction with FIG. 4. As shown in block 30 of FIG. 4, the method outlined in FIG. 4 includes identifying a plurality of classification regions within a classification matrix which is framed by ranges of values associated with one or more measurable parameters of particles that are configured for assay analysis. The measurable parameters may include fluorescence, light scatter, electrical impedance, or any other measurable property of the particles. In addition, the values associated with the one or more measurable parameters of the particles and framing the classification matrix may be of a scale which equates to the measurement scale for the particles or may be scale of values transformed from values of such a measurement scale. The latter embodiment may be particularly applicable when the classification matrix is framed by a scale of less granularity than the scale of values which may be measured from particles. Although three parameters are shown framing the classification matrices illustrated in FIGS. 2a and 2b, the process described in reference to FIG. 4 as well as all other methods described herein may be applied to classification matrices framed by any number of parameters. As described in more detail below, the process described in reference to FIG. 4 may in particular be applied to any classification matrices having classification regions which overlap.

The classification matrices depicted in FIGS. 2a and 2b include twelve classification regions. It is noted that the methods, storage mediums, and systems described herein may be applied to classification matrices having any number of classification regions, including but not limited to greater than 100 classification regions and, in some cases, greater than several hundred classification regions and possibly more. The number of classification regions depicted in FIGS. 2a and 2b is merely used to simplify the figures and emphasize the process steps of the method described in reference to FIG. 4. It is further noted that the method described in reference to FIG. 4 as well as all other methods described herein are not limited to instances in which classification regions are arranged non-uniformly within a matrix as depicted in FIGS. 2a and 2b. In particular, the method described in reference to FIG. 4 as well as all other methods described herein may be applied to classification matrices having uniformly distributed classification regions.

As shown in FIG. 2a, some of classification regions 1-12 overlap (i.e., regions 1 and 2; regions 4 and 5; regions 3, 6, and 7; and regions 10 and 11). More specifically, portions of classification regions 1-12 overlap as denoted by the double cross-hatching marks in FIG. 2a. It is noted that some classification regions may not overlap, such as illustrated with classification regions 8, 9, and 12 in FIG. 2a, but in other embodiments, all classification regions may overlap with at least one other classification region in the matrix. As shown in block 32 of FIG. 4, the method for configuring particle classification regions for an assay analysis system includes identifying unit locations within the classification matrix which are jointly assigned to two or more classification regions. In other words, the method may include identifying unit locations within the classification matrix at which two or more classification regions overlap. Alternatively stated, the method may include identifying unit locations within the classification matrix which fall into more than one classification region. The term "unit location" as used herein may refer to a specific coordinate point within a classification matrix. As such, it is conceivable that a classification region may have one or more than one unit location jointly assigned to another classification region.

In some cases, the method for configuring particle classification regions for an assay analysis system may include quantifying the number of jointly assigned unit locations as denoted in block 34 of FIG. 4. Such a process may be referred to herein as a "collision count process". Subsequent to quantifying the number of jointly assigned unit locations, a determination of whether the computed quantity is greater than a predetermined threshold may be made at block 36. If the computed quantity is greater than the predetermined threshold, the process continues to block 38 to adjust values of one or more dimensional attributes of one or more of the plurality of classification regions. The dimensional attributes may correspond to size, shape, angle, or any other parameter by which to characterize a classification region. As shown in FIG. 2a, classification regions 1-12 may, in some embodiments, be ellipsoidal. In such cases, block 38 in FIG. 4 may include adjusting values of at least one of a major axis, a minor axis, an elevation angle, and an azimuth angle of one or more of the plurality of classification regions. It is noted, however, that the methods, storage mediums, and systems described herein are not necessarily restricted to the shape of the classification regions depicted in the figures and, therefore, they are not restricted to being applied to classification matrices having elliptically shaped classification regions. In any case, the number of attributes and classifications regions and the magnitude of the adjustment/s affected by the process outlined in block 38 may generally be predetermined and may vary among systems and assay applications.

After dimensional attributes of one or more of classification regions 1-12 are adjusted in reference to block 38, the processes outlined in blocks 32, 34, 36, and 38 may be iteratively repeated until a quantity of jointly assigned unit locations less than or equal to the predetermined threshold is computed. Upon such an occurrence, the unit locations are reassigned as non-classification regions as denoted in block 40 in FIG. 4. Alternatively, the method may continue to block 40 after a first pass of block 36 when a quantity of jointly assigned unit locations less than or equal to the predetermined threshold is computed. The predetermined threshold may vary among systems and assay applications. In some embodiments, the number of iterations that the processes outlined in blocks 32, 34, 36, and 38 are repeated may be limited (i.e., the maximum number of iterations may be preset). In such cases, the iterative process may terminate either upon calculating a quantity of jointly assigned unit locations less than or equal to the predetermined threshold or until the preset number of iterations is met. In the latter case, it may generally be determined that the predetermined threshold is not attainable with the given set of classification regions and, thus, the method outlined in FIG. 4 may be terminated. At such a point, corrective action may be taken to select a different set of classification regions to process through the method outlined in FIG. 4 and/or lower the threshold by which the process outlined in block 36 is governed. It is noted that a limit on the number of iterations that blocks 32, 34, 36, and 38 may be repeated is not shown in FIG. 4 to simplify the drawing, but it is asserted that a skilled artisan would be appraised of how to incorporate such a limitation based on the aforementioned discussion.

In alternative embodiments, the method may not include comparing a quantity of jointly assigned unit locations to a predetermined threshold (i.e., the process described in reference to block 36). Rather, block 36 may be omitted from the flowchart depicted in FIG. 4 in some cases and, thus, the method may continue from block 34 directly to block 38. In such embodiments, the processes outlined in blocks 32, 34, and 38 may be repeated a predetermined number of times. Then, upon completion of the predetermined number of iterations, the configuration of classification regions having the smallest quantity of jointly assigned unit locations is selected and the associated jointly assigned unit locations are assigned as non-classification regions in block 40. Such an embodiment may be advantageous for seeking a set of classification regions having fewer jointly assigned unit locations relative to the set of classification regions originally set forth in reference to block 30 without having to be bound by a particular threshold. It is noted that the omission of block 36 and a limit on the number of iterations that blocks 32, 34, and 38 may be repeated is not shown in FIG. 4 to simplify the drawing, but it is asserted that a skilled artisan would be appraised of how to incorporate such a limitation based on the aforementioned discussion.

In yet other embodiments, the method may not include quantifying the number of jointly assigned unit locations (i.e., the collision count process described in reference to block 34)

or adjusting dimensional attributes of classification regions (i.e., the process described in reference to block 38). In particular, it is noted that the processes associated with blocks 34 and 38 are also optional and, therefore, may in some embodiments be omitted from the flowchart depicted in FIG. 4. Rather, a method for configuring particle classification regions for an assay analysis system may, in some embodiments, continue directly from block 32 to block 40. In some cases, however, it may be advantageous to compute the number of jointly assigned unit locations within a classification matrix and adjust dimensional attributes of the classification regions such that joint assignments may be minimized. In particular, it may be advantageous to retain a relatively large portion of the classification regions to insure that a relatively high classification efficiency may be attained.

In any case, the method may, in some embodiments, include reassigning unit locations neighboring the reassigned non-classification regions (i.e., the unit locations previously distinguished as being jointly assigned) as non-classification regions as denoted by block 42. Such a process may be performed subsequent or simultaneously with the process outlined in block 40. In general, the number of unit locations affected by the process outlined in block 42 may vary among systems and assay applications. For example, in some embodiments, the process denoted in block 42 may include only reassigning a set of unit locations directly bordering the non-classification regions assigned in reference to block 40 as non-classification regions. Such embodiments may be referred to herein as reassigning a single layer of neighboring unit locations relative to the border of the classification regions assigned in reference to block 40. In other cases, the process denoted in block 42 may include reassigning multiple layers of neighboring unit locations. In other words, the process denoted in block 42 may include reassigning as non-classification regions one or more sets of unit locations which laterally extend from the set of unit locations directly bordering the non-classification regions assigned in reference to block 40. In yet other embodiments, the method depicted in FIG. 4 may not include a process of reassigning neighboring unit locations. In particular, the process denoted in block 42 is optional and, thus, may be omitted from the flowchart depicted in FIG. 4 in some embodiments.

In general, the occurrence of misclassification lessens as more unit locations are reassigned as non-classification regions, but classification efficiency (ratio of particles classified to a population versus vs. particles classified to reject classes) drops as more regions are reassigned as non-classification regions. As such, there is a trade-off between minimizing a buffer region between classification regions and enlarging a buffer region. Optimization may generally depend on the system employed and assays to be analyzed.

The process of reassigning jointly assigned unit locations and, in some embodiments, neighboring unit locations is depicted in FIG. 2b. In particular, FIG. 2b depicts jointly assigned unit locations of classifications regions 1-2, 4-5, 3 & 6-7, and 10-11 reassigned as non-classification regions, which are denoted in FIG. 4 as white space in the classification matrix. In a sense, the jointly assigned unit locations of classifications regions 1-2, 4-5, 3 & 6-7, and 10-11 have been "carved out" such that the possibility of categorizing a particle to two different categories and/or categorizing a particle to an incorrect population is lessened or eliminated. In other words, the reassignment of the jointly assigned unit locations installs a buffer between classification regions. The benefit of the reassignment technique is that the regions can be made reasonably bigger without severely restricting the size of the classification regions.

As noted above, the methods, storage mediums, and systems described herein are not necessarily dependent upon the classification matrices and classification regions being graphically depicted in a physical sense. Thus, the process of reassigning jointly assigned unit locations does not necessarily need to depend on the depiction of the classification matrices, such as shown in FIGS. 2a and 2b. Rather, the process may be performed in a virtual sense, specifically scanning each point (i.e., unit location) of each classification region stored in memory. During such a scanning process, if a previously scanned region has already occupied that unit location (i.e., indicating a jointly assigned unit location), then the unit location may be reassigned as a non-classification point. In some cases, the reassignment process may include changing an identifier stored in the memory for the unit location. For example, the unit location may be originally assigned a number associated with its assigned categorization (e.g., 1-12) and then reassigned the numeral "0" to denote it as part of a non-classification region.

In other embodiments, a unit location identified as being jointly assigned may be reassigned a unique identifier, such as for example, −1. Such a unique identifier may help to differentiate the unit location from other non-classification points which were not originally assigned as classification regions, which may be helpful in cases in which points neighboring the unique identifiers may also be reassigned as non-classification regions as discussed above as an optional process with respect to block 42 in FIG. 4. In particular, the entire classification matrix may be searched and any points adjoining to a −1 identifier may be replaced with a −1 identifier, thus making the buffer larger. Alternatively, points adjoining a −1 identifier may be reassigned with a 0 identifier along with the points having the −1 identifier, so that the larger buffer may be classified as white space along with the other white space of the classification matrix.

As shown in FIG. 4, the method for configuring particle classification regions for an assay analysis system may, in some embodiments, terminate after block 40 or block 42. In other cases, however, an additional process which may be desirable to incorporate with the reassignment technique (i.e., the process of blocks 32 and 40 and sometimes block 42) is the determination of a classification efficiency of one or more of the classification regions. In particular, it may be advantageous to determine the classification efficiency of one or more classification regions after performing the reassignment technique to insure the reassignment process does not undesirably alter the classification regions so much that they are not representative of particle populations to be used in an assay. In addition or alternatively, it may be advantageous to determine the classification efficiency of one or more classification regions of the classification matrix before performing the reassignment technique to insure the process is applied to classification regions which are representative of particle populations to be used in an assay.

An exemplary technique for calculating the classification efficiency of one or more classification regions is denoted in blocks 44-48 in FIG. 4. In particular, block 44 involves the acquisition of data corresponding to measurable parameters of a plurality of particles. The data may be obtained by an assay measurement system and may, in some embodiments, include measurements of several different parameters including but not limited to those used to classify particles. For example, the data may include measurements of fluorescence, light scatter, electrical impedance, or any other measurable property of particles. In any case, the process may further include identifying unit locations within the classification matrix to which at least some of the data corresponds and calculating a classification efficiency of the plurality of particles relative to the plurality of classification regions as respectively noted in blocks 46 and 48 in FIG. 4. As noted above and depicted in FIG. 4, the calculation of classification efficiency (i.e., the processes associated with blocks 44-48) may be performed before and/or after the reassignment process (i.e., the processes associated with blocks 32 & 40 and sometimes block 42). In particular, FIG. 4 illustrates a continuation arrow from block 30 to block 44 for cases in which classification efficiency is calculated prior to the reassignment process. In addition, FIG. 4 illustrates a continuation arrow from block 42 (or block 40) to block 44 for cases in which classification efficiency is calculated after the reassignment process.

In some cases, the calculation of the classification efficiency may be used to determine whether dimensional attributes of the classification regions should be adjusted to try to achieve a higher classification efficiency. In particular, the method depicted in FIG. 4 may include determination block 50 at which if the calculated classification efficiency is determined to be less than a predetermined threshold, then the method continues to block 52 to adjust values of one or more dimensional attributes of one or more of the plurality of classification regions. The predetermined threshold may vary among systems and assay applications. In addition, the dimensional attributes may correspond to size, shape, angle, or any other parameter by which to characterize a classification region.

Subsequent to the adjustment of the one or more values, the method returns to block 46 to identify unit locations within the classification matrix having the adjusted classification regions to which at least some of the data acquired in block 44 corresponds and then continues to block 48 to calculate a new classification efficiency and compare it to the predetermined threshold in block 50. In some embodiments, the processes associated with blocks 46, 48, 50, and 52 may be iteratively repeated until a classification efficiency is calculated which meets or is above the predetermined threshold as shown in FIG. 4. In other embodiments, the number of iterations may be limited (i.e., the maximum number of iterations may be preset). In such cases, the iterative process may terminate either upon calculating a classification efficiency equal to or greater than the predetermined threshold or until the preset number of iterations is met. In the latter case, it may be generally determined that the predetermined threshold is not attainable with the given set of classification regions and, thus, the method outlined in FIG. 4 may be terminated. At such a point, corrective action may be taken to select a different set of classification regions to process through the method outlined in FIG. 4 and/or lower the classification efficiency threshold by which the process outlined in block 50 is governed. It is noted that a limit on the number of iterations that blocks 46, 48, 50, and 52 may be repeated is not shown in FIG. 4 to simplify the drawing, but it is asserted that a skilled artisan would be appraised of how to incorporate such a limitation based on the aforementioned discussion.

As shown in FIG. 4, upon achieving a classification efficiency equal to or greater than the predetermined threshold, the method may return to block 32 to initiate the reassignment process again, particularly in embodiments in which the adjustment process outlined in block 52 has been employed. In other cases, the method may continue to block 32 to start the reassignment process for the first time (i.e., if the reassignment process has not been conducted prior to the calculation of the efficiency). In yet other embodiments, the method may terminate upon achieving a classification efficiency equal to or greater than the predetermined threshold. In particular, it may be advantageous to terminate the method in cases in which the reassignment process has already been performed for the set of classification regions the classification efficiency is based upon (i.e., when the dimensional attributes of the classification regions have not been changed with respect to block 52). In any case, it is noted that provisions known to those skilled in the art may be incorporated within the method outlined in FIG. 4 such that toggling back and forth between the reassignment process and the calculation of the classification efficiency is not tied up in an excessively time consuming (or never-ending) cycle.

Another method for configuring classification regions for an assay analysis system is depicted in a flowchart in FIG. 5. It is noted that the methods described relative to FIGS. 4 and 5 are not necessarily mutually exclusive and, therefore, in some embodiments may be both used to configure classification regions for an assay analysis system. In general, the method described relative to FIG. 5 may be used to create classification regions which are characterized by values which more accurately correspond to measured values of particles. More specifically, the method described relative to FIG. 5 may be used to adjust one or more values of particle population categories to account for shifting of their corresponding classification regions when fitted within a classification matrix of lower precision than measured values of particles. As noted above, in some embodiments, classification matrices are often framed by scales of less granularity than the scale of values which may be measured from particles, specifically to reduce system memory capacity. For example, in some embodiments, classification matrices may be framed by ranges of integers computed from logarithmic values of measured parameters of particles. In some cases, however, converting measured values of particles to fit the logarithm scale of a classification matrix may skew the values, reducing the accuracy of particle classification. FIG. 3 illustrates a graphical representation of a classification matrix and a shift of classification regions resulting from processes outlined in FIG. 5 and, thus, FIG. 3 is discussed in conjunction with FIG. 5.

As noted above, a classification matrix is referred to herein as an array of values (actual or virtual) corresponding to measured parameters of particles used for classification. In addition, the term "classification region" as used herein refers to an area of a classification matrix to which a population of particles may be classified. The term "particle population category" differs slightly from the term "classification region" in that it refers to a grouping of possible measured values for one or more parameters of a particle population (i.e., with the term "particle population" referring to a set of particles having similar properties). In particular, the term "particle population category" refers to a grouping of possible values which are characterized by a measurement scale of one or more parameters of a particle population, while the values of a classification region are dependent on the range of values and granularity of the classification matrix in which they are arranged.

For example, in embodiments in which median fluorescence intensity (MFI) is used to classify particles of an assay, a grouping of possible MFI values for a particle population may be referred to as the particle population category. Conversely, a classification region of a classification matrix corresponding to such a particle population category may include the same values or different values depending on the range of values and granularity of the classification matrix. In particular, if a classification matrix is framed by the same values and granularity as the MFI scale used to measure the particles, then the range of values comprising the classification region will be the same as the values of the corresponding particle population category. In contrast, if a classification matrix is framed by different values and/or granularity as the MFI scale used to measure the particles, then the range of values comprising the classification region will be different from the values of the corresponding particle population category.

As shown in FIG. 5, a method for configuring classification regions for an assay analysis system may include block 60 in which one or more values that correspond to a point within an assay particle population category are mathematically transformed into new values. As used herein, the term "mathematically transforming" may generally refer to applying a mathematical formula to change a value to a different value. Any formula may be considered and may generally depend on the desired granularity of the classification matrix relative to the measurement scale for acquiring data on the particles. Some exemplary formulas may be logarithmic based formulas; formulas employing an exponential, a power, a binomial, a Taylor or MacLaurin series, a parametric equation, a coordinate transformation; or relatively less complex formulas where each point is multiplied by or added to a constant. Other formulas may also be considered for the process outlined in block 60. Consequently, although the exemplary mathematical processes discussed with respect to Tables 1 and 2 below in reference to the method outlined in FIG. 5 utilize a logarithmic based formula for such a process, the method recited in FIG. 5 is not necessarily so limited.

As noted above, a particle population may be characterized by one or more measurement parameters and, thus, a point within a particle population category may be characterized by one or more values. For instance, the exemplary mathematical processes discussed with respect to Table 1 below in reference to the method outlined in FIG. 5 describes particle population categories characterized by three parameters, denoted as classification channels "CL1", "CL2", and "CL3". Consequently, the process outlined in block 60 may include mathematically transforming one or more values corresponding to a point within an assay particle population category.

In general, the point within an assay particle population category corresponding to the process outlined in block 60 may correspond to any point within the configured assay particle population category. In some embodiments, it may be advantageous for the point to be a central point of the assay particle population category. In particular, particle populations are often created by dyeing them with target amounts of dyes, which are based on central points of assay particle population categories. In some cases, however, it may be advantageous for the point to be a non-central point, particularly if the particle population is expected to be lopsided relative to the grouping of values encompassed by the assay particle population category. In such cases, a non-central point of a particle population category may be the basis to which to dye a particle population rather than a central point. In any case, converting measured values of particles to fit a classification matrix having lower granularity may skew the values. As a result, a target dye amount may not directly correlate with a particular point (e.g., a center) of a classification region. As such, the method presented in FIG. 5 may be particularly beneficial for adjusting a target dye amount for a population of particles. In other cases, points of a particle population category which are not necessarily associated with dying a particle population may be considered for the process outlined in block 60. An example of such a point may include but is not limited to a point along the outer periphery of the classification region.

Subsequent to mathematically transforming the one or more values in reference to block 60, the one or more mathematically transformed values are respectively converted to one or more first integers, the one or more first integers are mathematically transformed, and the resulting one or more values are respectively converted to one or more second integers as respectively denoted in blocks 62, 64, and 66. The conversion of values to the first and second integers may include rounding or truncating the values. In general, the formula used to mathematically transform the one or more first integers for the process outlined in block 64 may be the inverse of the formula used to mathematically transform the one or more values in reference block 60. For example, if a logarithmic based formula is used to mathematically transform the one or more values for the process outlined in block 60, then an anti-logarithmic based formula of the same base may be used to mathematically transform the one or more first integers in reference to block 64 or vice versa. Furthermore, if a formula including an expression raised to a particular positive power is used to mathematically transform the one or more values for the process outlined in block 60, then a formula including an expression raised to a negative to that number may be used to mathematically transform the one or more first integers in reference to block 64 or vice versa. Moreover, if a formula including multiplication by a constant is used to mathematically transform the one or more values for the process outlined in block 60, then a formula including division by the same constant may be used to mathematically transform the one or more first integers in reference to block 64 or vice versa.

In any case, subsequent to the process outlined in block 66, the method continues to block 68 at which the one or more second integers are respectively designated as one or more replacement values for the point within the assay particle population category referenced in block 60. In some embodiments, the method may additionally or alternatively include designating the one or more second integers as targets for dyeing particle populations as denoted in block 70. Such a process, however, is optional and, thus, block 70 may be omitted from FIG. 5 in some embodiments. In particular, it may be noted that one or more of the second integers are relatively close (e.g., the difference being less than the precision by which particles may be dyed) to one or more original values for the point within the assay particle population category and, thus, changing the target for dyeing a particle population may be unnecessary. In any case, once one point of an assay particle population category is changed and, thus, a corresponding unit location of a classification region is skewed from its original location, other points within a classification region will shift in the same direction and magnitude based upon a known configuration (i.e., size, shape, dimensions) of a classification region. An exemplary shifting effect is illustrated in FIG. 3 for a plurality of classification regions.

As shown in FIG. 5, the method may, in some embodiments, be routed to block 72 after block 68 or 70 to determine whether there are any other assay particle population categories to be evaluated. If the determination is affirmative, the method returns to block 60 to mathematically process one or more values corresponding to a point within a different assay particle population category and further performs the processes outlined in block 62-68 and sometimes block 70 for the different assay population category. Such processes may be reiterated for any number of assay particle population categories and, in some cases, reiterated for all assay particle population categories considered for an assay. Upon determining no other assay particle population categories are to be evaluated at block 72, the process may terminate or be routed to block 74 to start an optional assessment process, which is described in more detail below in reference to blocks 74-88. In an alternative process, the sequence of mathematical processes described with respect to blocks 60-68 may be performed simultaneously for a plurality of assay particle population categories.

As set forth in more detail below, the optional assessment process described in reference to FIG. 5 (i.e., blocks 74-88) may be conducted after a plurality of replacement values have been designated for a plurality of assay particle population categories. In other embodiments, however, the optional assessment process may be conducted after one or more replacement values have been designated for a single assay particle population category. To reflect the latter embodiment, FIG. 5 includes a connection arrow between blocks 70 and 74, which may alternatively serve as a connection arrow between blocks 68 and 74 if the process associated with block 70 is omitted from the method. In either case, additional assay particle population categories may be evaluated (i.e., values corresponding to points within assay particle population categories may be mathematically adjusted to designate replacement values for points) after the optional assessment process is conducted and therefore, there is a connection arrow in FIG. 5 between blocks 82 and 72 to denote such an option. In other embodiments, the optional assessment process may be foregone and, thus, blocks 74-88 may be omitted from FIG. 5 in some cases.

In general, the optional assessment process may be used to determine how well the second integer fits the scale of the classification matrix such that resulting a classification region may accurately correspond to measured values of a particle population. As shown in FIG. 5, block 74 includes mathematically transforming the one or more second integers by applying the formula used to mathematically transform the one or more values in reference block 60. The process outlined in block 74 may be performed directly subsequent to the process described in reference to block 70 or may be performed upon determining no other assay particle population categories are to be evaluated in block 72. In either case, after block 74, the method continues to block 76 at which difference/s between the value/s resulting from mathematically transforming the second integer/s and their nearest integer/s are calculated. Subsequent thereto, the assessment process is routed one of two ways at block 78 as set forth below.

In cases in which a single assay particle population category has been evaluated and one or more of its values have been replaced with one or more second integers computed in block 66 or when it is desirable to perform the assessment process for each individual assay particle population category, the method may continue to block 80 to determine whether the difference/s calculated at block 76 are greater than a predetermined threshold. The predetermined threshold may vary among systems and assay applications. As shown in block 82 of FIG. 5, if the computed difference/s are greater than the predetermined threshold, the designation of the second integer/s as replacement value/s in block 68 is revoked. In particular, a difference greater than a predetermined threshold may be indicative that a corresponding second integer does not better represent measured values of a particle population for the classification region and, thus, it may not be beneficial to adjust the point within the assay particle population category to such a number. In contrast, if the computed difference/s are less than the predetermined threshold, the designation of the second integer/s as the replacement value/s for the point within the assay particle population category remains.

In alternative embodiments, the method may not include comparing the difference/s calculated at block 76 to a predetermined threshold (i.e., the process described in reference to block 80). Rather, block 80 may be omitted from the flowchart depicted in FIG. 5 in some cases. In its place, a process of calculating difference/s between the value/s resulting from the mathematical transformations performed in reference to block 60 and their nearest integer/s may be calculated. Upon determining such difference/s are less than the difference/s computed in reference to block 76, the method may continue to block 82 to revoke the designation of the second integer/s as replacement value/s in block 68 is revoked. It is noted that the omission of block 80 and the replacement of blocks representing the aforementioned processes are not shown in FIG. 5 to simplify the drawing, but it is asserted that a skilled artisan would be appraised of how to incorporate such a limitation based on the aforementioned discussion.

In any case, the method may be routed to block 72 to determine whether there are any other assay particle population categories to be evaluated subsequent to the assessment processes noted above. The sequence of steps associated with blocks 60-76 and the assessment process noted above may be reiterated any number of times to evaluate points within different assay particle population categories. Upon determining no other assay particle population categories are to be evaluated, the process may be terminated. In alternative embodiments, the method may be routed to block 76 from the assessment processes noted above, particularly if a plurality of assay particle population categories has been evaluated prior to the assessment process. In yet other embodiments, the process may terminate at block 80 upon determining the computed difference is less than the predetermined threshold, after determining difference/s between the value/s resulting from the mathematical transformations performed in reference to block 60 and their nearest integer/s is greater than differences computed in reference to block 76, or at block 82 upon revoking the designation of the second integer as the replacement value. None of such termination scenarios, however, are shown in FIG. 5 to simplify the drawing.

In cases in which points within multiple assay particle population categories have been evaluated and replaced with second integers computed in block 66 prior to the optional assessment process, the method may continue from block 78 to block 84 to calculate a percentage of the differences calculated for each of the second integers that are above a predetermined threshold. The predetermined threshold may vary among systems and assay applications and may be the same or different from the predetermined threshold referenced in block 80. Thereafter, the method continues to block 86 to determine whether the percentage is greater than a preset level. The preset level may vary among systems and assay applications. As shown in block 88 of FIG. 5, if the percentage is greater than the preset level, the designation of the second integers as replacement values described in reference to block 68 is revoked. In particular, a percentage greater than a preset level may be indicative that a significant number of second integers do not better represent measured values of particles for their respective assay particle population categories and, thus, it may not be beneficial to adjust the points within the assay particle population categories to such numbers. In contrast, if the computed percentage is less than the preset level, the designation of the second integers as replacement values for the classification regions remains. In either case, the process may terminate after block 86 or 88 as shown in FIG. 5. Alternatively, the process may return to block 72 to determine if there are any other assay particle population categories to be evaluated. Such an option is not shown in FIG. 5 merely to simplify the drawing.

In alternative embodiments, the method may not include calculating a percentage of the differences that are above a predetermined threshold (i.e., the process described in reference to block 84). Rather, block 84 may be omitted from the flowchart depicted in FIG. 5 in some cases. In its place, a process of calculating difference/s between the values resulting from the mathematical transformations performed in reference to block 60 and their nearest integers may be calculated. At such a point, a percentage of the differences that are less than the differences computed in reference to block 76 may be computed. In some cases, such a percentage may be compared to a preset level as described in reference to block 86 and the method may either proceed to block 88, terminate, or return to block 72. It is noted that the omission of block 86 and the replacement of the aforementioned process are not shown in FIG. 5 to simplify the drawing, but it is asserted that a skilled artisan would be appraised of how to incorporate such a limitation based on the aforementioned discussion.

Regardless of how the assessment process is employed, it may only be pertinent to relatively large values corresponding to the point within the assay particle population category described in reference to block 60. In particular, in cases in which the method outlined in FIG. 5 only varies the values by up to a few percentage points, such a variance may not be significant enough for the relatively small values. In view of this, provisions may be incorporated into the method outlined in FIG. 5 to only implement the assessment process for values corresponding to the point within the assay particle population category described in reference to block 60 above a a particular number. Alternatively, provisions may be implemented such that the assessment process is applied to an entire range of values, but the revoking processes of blocks 82 and 88 are ignored for values less than a particular number. It is noted that such provisions are not shown in FIG. 5 to simplify the drawing, but it is asserted that a skilled artisan would be appraised of how to incorporate such a limitation based on the aforementioned discussion.

An optional process which may be added to the method outlined in FIG. 5 is to repeat the processes discussed with respect to blocks 60-76 using a different set of mathematical transform equations and then compare the differences calculated in reference to block 76 for each set of mathematical transform equations used to evaluate the particle population categories. At such a point, the second integers produced from the set of mathematical transform equations producing the smallest variance of differences may be designated as the final replacement values for the point within the assay particle population category referenced in the process outlined in block 60. In particular, the second integers produced from the set of mathematical transform equations producing the smallest variance of differences may be representative of values which may most accurately correspond to measured values of particles in a classification matrix framed by a scale of parameters based on the set of mathematical transform equations. It is noted that such an optional process is not depicted in FIG. 5 to simplify the drawing, but it is asserted that a skilled artisan would be appraised of how to incorporate the process based on the aforementioned discussion.

Exemplary mathematical processes which may be used for the processes discussed with respect to blocks 60-88 of FIG. 5 are described below. In addition, data generated and used from such exemplary processes are shown in Tables 1 and 2. In particular, Tables 1 and 2 list data generated for three assay particle population categories, specifically classification data for three classifications channels of each assay particle population category denoted as "CL1", "CL2", and "CL3". It is noted that a multiplexed system may and will typically include more than three assay particle population categories. In addition, fewer or more than three classification channels may be used to classify particles, depending on the assay analysis system employed. Thus, the process described in reference to FIG. 5 should not be construed to be limited to the exemplary data provided in Tables 1 and 2. Classifications channels CL1-CL3 may generally refer to any parameter by which to classify particles, but in some embodiments may specifically refer to fluorescence measurements. In such cases, the method outlined in FIG. 5 may be particularly applicable for changing the target amount for dyeing a particle population. Table 1 specifically refers to the processes outlined in blocks 60-70 of FIG. 5 and Table 2 specifically refers to the assessment process discussed with respect to blocks 76-88 of FIG. 5 as well as alternative options for the assessment process.

TABLE 1

Exemplary Data Generation for Configuring Classification Regions for an Assay Analysis System using the Process Depicted in FIG. 5

|   | MFI Targets | | | Transform Formula | | | Rounded $1^{st}$ Integers | | | Inverse Transform Formula | | | Rounded $2^{nd}$ Integers | | |
|---|---|---|---|---|---|---|---|---|---|---|---|---|---|---|---|
|   | CL1 | CL2 | CL3 | CL1 | CL2 | CL3 | CL1 | CL2 | CL3 | CL1 | CL2 | CL3 | CL1 | CL2 | CL3 |
| 1 | 18.85 | 30.99 | 10.59 | 73.29 | 84.99 | 60.09 | 73.00 | 85.00 | 60.00 | 18.62 | 31.00 | 10.55 | 19.00 | 31.00 | 11.00 |
| 2 | 691.74 | 985.68 | 341.37 | 160.38 | 169.07 | 143.06 | 160.00 | 169.00 | 143.00 | 680.11 | 982.07 | 339.55 | 680.00 | 982.00 | 340.00 |
| 3 | 7113.71 | 1077.04 | 264.63 | 217.54 | 171.24 | 136.81 | 218.00 | 171.00 | 137.00 | 7247.63 | 1065.59 | 265.65 | 7248.00 | 1066.00 | 266.00 |

TABLE 2

Exemplary Data Generation for Assessing the Classification Regions Configured
for an Assay Analysis System using the Process Depicted in FIG. 5

| | Transform Formula on $2^{nd}$ Integers | | | Rounded 3rd Integers | | | Differences | | | Differences relating to $1^{st}$ Transform Formula | | |
|---|---|---|---|---|---|---|---|---|---|---|---|---|
| | CL1 | CL2 | CL3 | CL1 | CL2 | CL3 | CL1 | CL2 | CL3 | CL1 | CL2 | CL3 |
| 1 | 73.47 | 85.00 | 60.94 | 73.00 | 85.00 | 61.00 | 0.47 | 0.00 | 0.06 | 0.29 | 0.01 | 0.09 |
| 2 | 16.00 | 169.00 | 143.03 | 16.00 | 169.00 | 143.00 | 0.00 | 0.00 | 0.03 | 0.38 | 0.07 | 0.06 |
| 3 | 218.00 | 171.01 | 137.03 | 218.00 | 171.00 | 137.00 | 0.00 | 0.01 | 0.03 | 0.46 | 0.24 | 0.19 |

The first three columns denoting data for the CL1-CL3 channels in Table 1 include the MFI targets for the respective assay particle population categories. For the example presented in Table 1, the targets are based upon a MFI scale of 1 to 32,767, but it is noted that larger or smaller scales and/or different parameters may be used for the targets. In some embodiments, the targets may refer to values corresponding to central points within the respective assay particle population categories. In other cases, however, the targets may refer to other points within the assay particle population categories. The next three columns in Table 1 include values resulting from mathematically transforming the MFI targets in a logarithmic based formula (referred to in Table 1 as "Transform Formula"). Such a mathematical process refers to block 60 of FIG. 5. An exemplary logarithmic based formula which may be employed is $C*\log_{10}(MFI_{Target}+1)$ where $C=255/\log_{10}(32,767)$. Other logarithmic based formulas or non-logarithmic based formulas, however, may be used depending on the system and assay application. The values resulting from the logarithmic based formula are converted to first integer values in the next three columns of Table 1, specifically by rounding the values for the example presented in Table 1. In alternative embodiments, the values may be truncated. Such a mathematical process refers to block 62 of FIG. 5.

Subsequent to converting the values resulting from the logarithmic based formula to first integer values, the first integers are mathematically transformed in an anti-logarithmic based formula (referred to in Table 1 as "Inverse Transform Formula"). Such a mathematical process refers to block 64 of FIG. 5. An exemplary anti-logarithmic based formula which may be employed is $10^{[first\ integer/C]}-1$. Other anti-logarithmic based formulae or non-anti-logarithmic based formulas, however, may be used depending on the system and assay application. The values resulting from the anti-logarithmic based formula are converted to second integer values in the last three columns of Table 1, specifically by rounding the values for the example presented in Table 1. In alternative embodiments, the values may be truncated. Such a mathematical process refers to block 66 of FIG. 5. As noted above in reference to block 68 of FIG. 5, the second integers are designated as the replacement values for the points of the assay particle population categories referred to in block 60, which in the example presented in Table 1 refers to the MFI targets. In some embodiments, the second integers may be further designated as the target values for dying different particle populations for assay analysis, specifically corresponding to block 70 in FIG. 5.

As noted above, the process outlined in block 70 is optional and, thus, may be omitted from the example presented in Table 1 in some embodiments. In particular, it may be noted that one or more of the second integers are relatively close (e.g., the difference being less than the precision by which particles may be dyed) to one or more original values for the point within the assay particle population category and, thus, changing the target for dyeing a particle population may be unnecessary. For instance, in regard to the exemplary mathematical processes discussed with respect to Table 1 below, it has been discovered that changing targets for dyeing particle populations is really only prudent for particle population categories having MFI targets greater than approximately 200. This is generally due to an estimation that the sequence of mathematical processes described with respect to Table 1 generates second integers which vary by up to approximately 2% from the values of their original MFI targets. In particular, a variance of an MFI target by up to 2%, is not very significant for the smaller target numbers, particularly given the precision of most dying techniques. A 2% variance, however, may be significant for the larger MFI targets. Based on this, provisions may be included in the process outlined in block 70 of FIG. 5 to only implement the designation of the second integers as targets for dyeing particle populations for particle population categories having original MFI targets greater than a predetermined threshold, such as greater than 200, for example. Using such a provision, the designation of second integers for classification region 1 noted in Table 1 may not be implemented, particularly since its MFI targets for all three channels CL1-CL3 are less than 200.

As further noted above in reference to FIG. 5, the process outlined therein may, in some embodiments, include an assessment process to determine how well a second integer fits the logarithm scale of the classification matrix, which in turn reflects how accurately resulting classification regions may correspond to measured values of a particle population. Examples of mathematically processes that may be involved in such assessment process are shown in Table 2. In particular, the first three columns in Table 2 include values resulting from mathematically processing the second integers of the last three columns in Table 1 in a logarithmic based formula. Such a process refers to block 74 in FIG. 5. In general, the logarithmic based formula may be similar to the formula used for the processing the MFI targets with the exception that the value of the MFI target in the formula is replaced with the second integer. For example, an exemplary logarithmic based formula which may be employed for the example of Table 1 is $C*\log_{10}(second\ integer+1)$ where $C=255/\log_{10}(32,767)$.

As set forth above with respect to block 76 of FIG. 5, a difference between the values resulting from the logarithmic based formula used in the assessment process and their nearest integers may be calculated. As such, the values resulting from the logarithmic based formula in the first three columns of Table 2 are converted to third integer values in the next three columns of Table 3, specifically by rounding the values for the example presented in Table 2. In alternative embodiments, the values may be truncated. The next three columns in Table 2 denote the absolute value of the differences between the first set of three columns and the second set of three columns in Table 2. Such a mathematical process refers to block 74 in FIG. 5. In some cases, the computed differences may be compared to a predetermined threshold to determine how well the second integers computed for each of the assay particle population categories fits a logarithm scale of the classification matrix as noted in block 80 of FIG. 5. In general, the predetermined threshold may vary among systems and assay applications. An exemplary predetermined threshold may be approximately 0.25, for example. Using such a threshold, it is noted that all of the second integers presented in Table 2 except for the CL1 value of region #1 may be deemed to fit well within the logarithm scale of the classification matrix.

The CL1 value of region #1 has a computed difference of 0.47. Based on this, the designation of the second integer value of 19.00 for the MFI target value of the CL1 value of region #1 may be revoked as noted in block 82 of FIG. 5. In some embodiments, however, the designation may not be revoked since the MFI target for the CL1 channel of region #1 is less than 200. In particular, as noted above in reference to FIG. 5, provisions may be implemented into the assessment process such that the revoking processes of blocks 82 and 88 are ignored for values less than a particular number. As noted above, with regard to designating the second integers of Table 1 for a dyeing targets for particle populations, such dyeing designations may be futile for MFI targets less than 200 This is generally due to an estimation that the sequence of mathematical processes described with respect to Table 1 generates second integers which vary by up to approximately 2% from the values of their original MFI targets. For the same reasons, a level at which to implement provisions to ignore the revoking processes of blocks 82 and 88 for the exemplary assessment process outlined in Table 2 may be MFI targets less than 200. Alternatively, provisions may be incorporated into the example presented in Tables 1 and 2 to only implement the assessment process for MFI targets above 200.

An alternative route for the assessment process is to calculate a percentage of differences calculated for a plurality of assay particle population categories that are above a predetermined threshold as shown in block 84 of FIG. 5 and compare the calculated percentage to a preset level as shown in block 86 of FIG. 5. In general, the predetermined threshold and preset level may vary among systems and assay applications. An exemplary predetermined threshold for the calculated differences may be approximately 0.25 and an exemplary preset level for the calculated percentage may be approximately 10%, for example. Using such a predetermined threshold and preset level, it is noted that the second integers presented in Table 1 may be revoked as being replacement values for the MFI targets of classification channels CL1-CL3 for regions 1-3. In particular, since CL1 value of region #1 has a computed difference of 0.47 and it accounts for approximately 11% of the values, then all of the second integers may be revoked as replacement values. Alternatively, provisions may be implemented that ignore the computed differences for MFI targets of region #1 since the values of the MFI targets are less than 200 and, thus, in such cases, the replacement of the second integers for MFI targets of at least regions #2 and #3 may be retained.

As noted above, in regard to FIG. 5, an alternative sequence of processes may be used for the assessment process described therein. In particular, rather than comparing the differences calculated for the transformation of the second integers and their nearest integers to predetermined thresholds, an assessment process may include comparing the differences to differences relating to the values resulting from transforming the MFI targets and their nearest integers. Such a process is denoted in the last three columns of Table 2. In particular, the last three columns in Table 2 computes the absolute values for the differences between the values resulting from transforming the MFI targets and their nearest integers from Table 1 (i.e., the values in the second and third sets of three columns in Table 1). Upon comparing the different sets of columns relating to computed differences in Table 2, any differences in the last set of three columns which are less than the differences in the previous set of three columns may cause the designation of the second integers of corresponding channels and regions as replacement values for MFI targets to be revoked. Based on this, it is noted that all of the second integers presented in Table 2 except for the CL1 value of region #1 may be retained as replacement values for their MFI targets. As noted above, provisions may be implemented into such an assessment process to only implement the assessment process for MFI targets above 200 and, thus, in such cases, the notation of the smaller difference for CL1 channel or region #1 may not be of significance.

Figure 6:
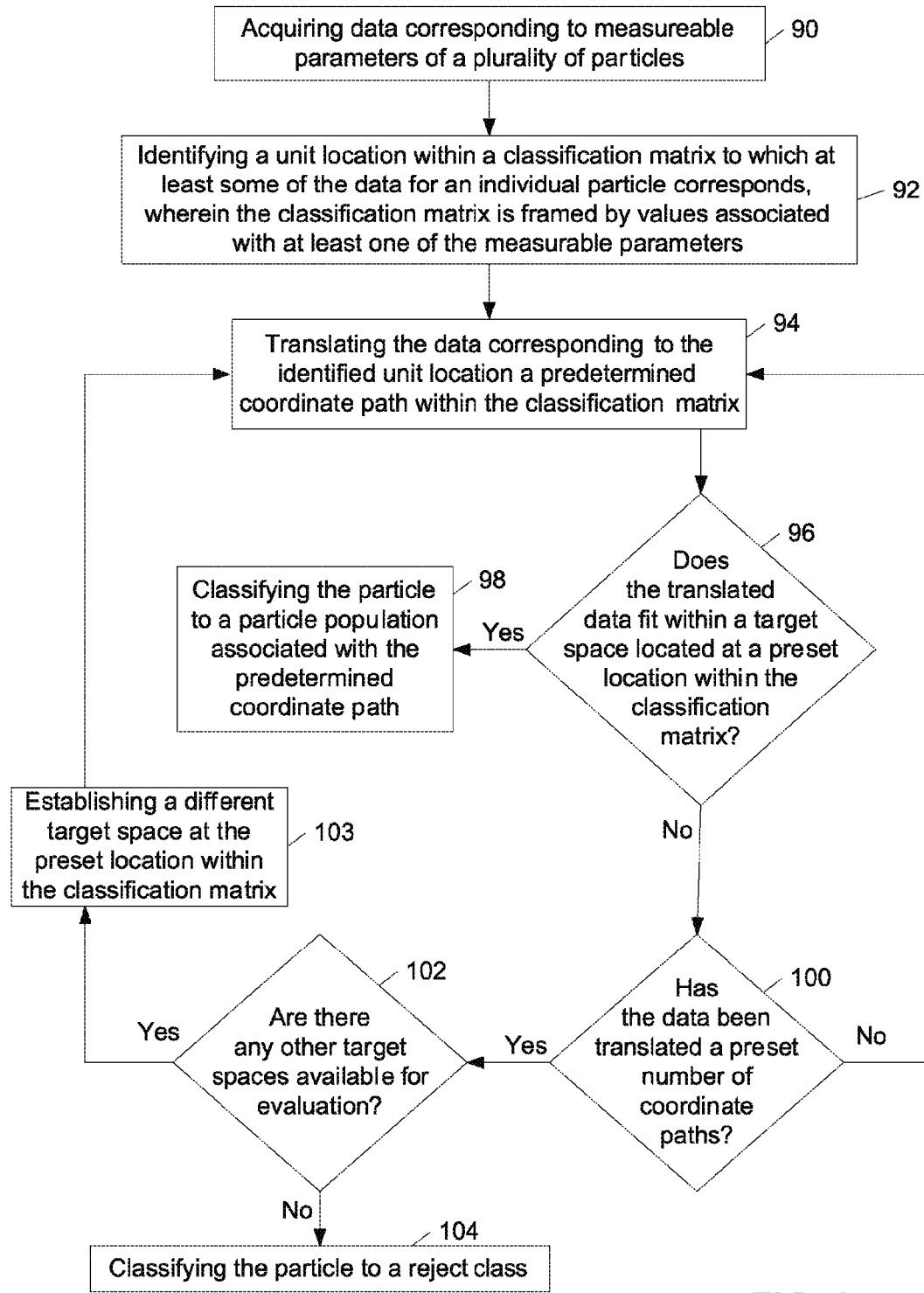
FIGS. 6 and 7 illustrate flowcharts of exemplary methods for classifying particles of an assay.
Figure 8:
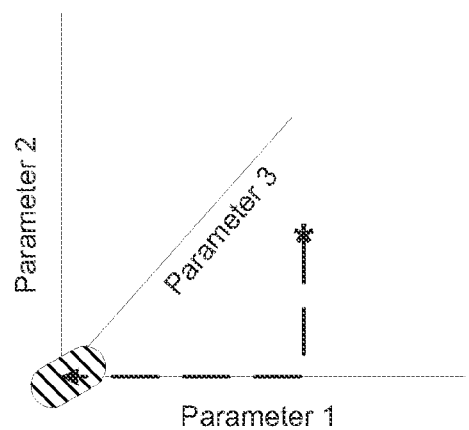
FIGS. 8 and 9 illustrate graphical representations of classification matrices used for describing the processes outlined in FIGS. 6 and 7.
Figure 9:
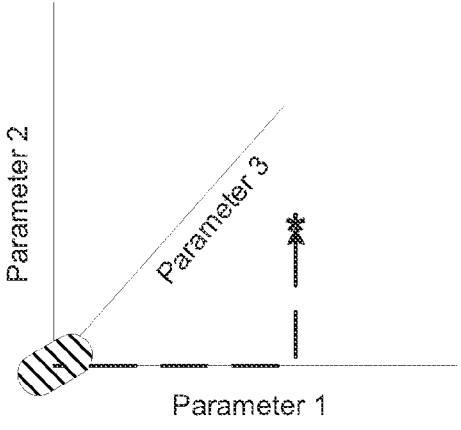
Figure 10:
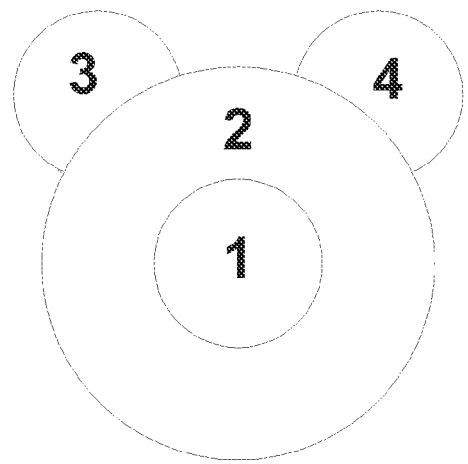
FIG. 10 illustrates an exemplary target space representing multiple classification region configurations stacked upon each other which is used to explain the processes described in reference to FIGS. 11 and 12.

As noted above, FIGS. 6, 7, 11, and 12 depict flowcharts of methods for classifying particles of an assay. FIGS. 8-10 illustrate graphical representations of classification matrices and target spaces which are used to help explain the processes outlined in FIGS. 6, 7, 11, and 12 and, thus, FIGS. 8-10 are discussed in conjunction with such figures. As shown in FIG. 6, a method for classifying particles may include block 90 in which data corresponding to measurable parameters of a plurality of particles is acquired. The data may be obtained by an assay analysis system and may, in some embodiments, include measurements of several different parameters including but not limited to those used to classify particles. For example, the data may include measurements of fluorescence, light scatter, electrical impedance, or any other measurable property of particles. The process may further include identifying a unit location within a classification matrix to which at least some of the acquired data for an individual particle corresponds as noted in block 92 of FIG. 6. In addition, the method may include block 94 in which the data corresponding to the identified unit location is translated a predetermined coordinate path within the classification matrix. The predetermined coordinate path may generally be characterized by a number of units for each axis of the classification matrix. Furthermore, translating the data corresponding to the identified unit location may generally refer to moving the data point the prescribed number of units relative to the identified unit location. For example, if the predetermined coordinate path is (1, 2, 3), the data point will be moved 1 unit along the x-axis of the classification matrix, 2 units along the y-axis of the classification matrix, and 3 units along the z-axis of the classification matrix. FIG. 8 depicts an exemplary graphical representation of an identified unit location within a classification matrix that is translated a predetermined coordinate path (i.e., the identified unit location is denoted by an asterisk and the coordinate path is denoted by a dotted line). FIG. 8 further shows a target space located near the origin of the classification matrix (i.e., the target space denoted as the cross-hatched elliptical region). As set forth in more detail below, a target space is used for the method outlined in FIG. 6 to classify particles to a particular particle population based on the coordinate path a data point is translated from its unit location to the target space.

In some cases, the process of identifying a unit location within a classification matrix may further include identifying a segment or node of the classification matrix comprising the unit location. In general, a segment or a node of a classification matrix may refer to an area of a classification matrix including a plurality of unit locations but differs from the term "classification region" in that the segment or node does not necessarily correspond to a particle population category for an assay. An exemplary classification matrix may be segmented into sections of equal area, such as quadrants, for instance. Any number, size, and shape of nodes, however, may be considered for segmenting a classification matrix. In any case, translating the data from an identified segment of a classification matrix may include translating the data a predetermined coordinate path which is associated with the identified segment. Such a technique may reduce the number of coordinate paths considered for fitting the data point to the target space (a process which is described in more detail below in reference to blocks 96 and 100) and, thus, may save processing time. It is noted, however, that identifying a segment or node of a classification matrix comprising the unit location is an optional process for the method described in reference to FIG. 6 and, thus, may be omitted in some embodiments.

In any case, subsequent to translating the data, a determination is made at block 96 as to whether the translated data fits within a target space located at a preset location of the classification matrix. The preset location may be any location within the classification matrix. In some embodiments, the preset location may include the origin of the axes framing the classification matrix and in specific cases the target space may be centered at the origin. As used herein, the term "target space" may generally refer to a bounded area having a periphery which is indicative of one or more classification region configurations stacked upon each other. The term "classification region configuration" as used herein refers to a set design of a classification region as characterized by its shape, size, etc. It is noted that a classification region configuration is not necessarily specific to a single classification region within a classification matrix. In particular, more than one classification regions of a classification matrix may have the same classification region configuration. In other words, different classification regions of a classification matrix may have uniform dimensions. As such, the distinction of whether the target space represents a single classification region configuration or multiple classification region configurations does not parallel whether the target space represents a single or multiple classification regions.

It is further noted that a target space differs from a classification region in that its coordinate location within a classification matrix does not necessarily correspond to measured values for a particle population even if the bounded area only represents a single classification region configuration. In particular, as set forth in more detail below with respect to FIG. 8, a target space is used to classify particles to a particular classification region based on the coordinate path a data point is translated from its unit location to the target space rather than merely fitting the data point into a classification region arranged at its unit location.

In general, the target space may be of any configuration (i.e., size, shape, etc.) which is representative of one or more classification region configurations stacked upon each other. In some embodiments, the target space may be representative of a single classification region configuration. In other words, the target space may include a periphery of a single classification region configuration. Alternatively, the target space may be representative of multiple classification region configurations stacked upon each other. In other words, the target space may include a periphery of multiple region configurations centered about the same point. Exemplary processes for determining if and which of such multiple classification region configurations a data point may be translated to when conducting the method set forth in FIG. 6 are outlined and described in more detail below with respect to FIGS. 11 and 12 in addition to the description provided with respect to FIG. 8 of the general concept of translating data to a target space for classifying a particle.

As shown in block 98 of FIG. 6, if the data translated in reference to block 94 fits within the target space referenced in block 96 using a given predetermined coordinate path, the particle is classified to a particle population associated with the predetermined coordinate path. Such an association may be retrieved from a database or look-up table which is accessible and, in some cases, stored by the storage medium and/or system performing the process. FIG. 8 depicts an exemplary graphical representation of data translated from an identified location and fitting into a target space. On the contrary, if the data translated in reference to block 94 does not fit within the target space referenced in block 96 using a given predetermined coordinate path, the process continues from block 96 to block 100 at which a determination is made as to whether the data has been translated a preset number of different coordinate paths. The preset number of coordinate paths may vary among systems and assay applications. As shown in FIG. 6, if the data has not been translated a preset number of different coordinate paths, then the process returns to block 94 to translate the data a different and new coordinate path. Such a process may be iteratively repeated until one of two conclusive actions is conducted. In particular, the process may be iteratively repeated until the translated data fits within the target space and, thus, continues to block 98 or the preset number of coordinate paths has been exhausted without determining the translated data fits within the target space. The latter action is depicted in FIG. 6 following the "yes" connection arrow extending from block 100 to block 102.

As shown in FIG. 6, a determination is made at block 102 regarding whether any other target spaces (i.e., target spaces of different configurations) are available for evaluation. If additional target spaces are available for evaluation, the method continues to block 103 to establish a different target space at the preset location within the classification matrix. Subsequent thereto, the method returns to block 94 to translate the data corresponding to the identified unit location of the classification matrix a predetermined coordinate path and further onto block 96 to determine whether the translated data fits the different target space. The sequence of processes described in reference to blocks 94-102 may be iteratively repeated until a particle is classified to a particle population or until no other target spaces are available for evaluation. Upon determining no other target spaces are available for evaluation at block 102, the method may include classifying the particle to a reject class as denoted in block 104.

In general, any number of target spaces may be used for the classification technique outlined in FIG. 6, including between one and the number of particle populations included within an assay. In some embodiments, it may be advantageous to have target spaces of different configurations available for evaluation such that classification regions of non-uniform dimensions may be considered. In particular, the more target spaces available for evaluation allows for greater variability in classification region configurations, which may in turn better represent different particle populations within an assay and result in higher collection efficiencies. A disadvantage of having more target spaces available for evaluation is the amount of memory needed to store the configurations of each target space. As such, in some embodiments, it may be advantageous to limit the number of target spaces available for evaluation for the classification technique outlined in FIG. 6. As described in more detail below, the techniques outlined in FIGS. 11 and 12 help reduce memory storage requirements when a target space representing multiple classification region configurations is used and, consequently, such techniques may be particularly advantageous to employ in some cases. The techniques discussed in reference to FIGS. 11 and 12 may also be used for the method outlined in FIG. 7 and, thus, are described subsequent to the description of FIG. 7.

Figure 7:
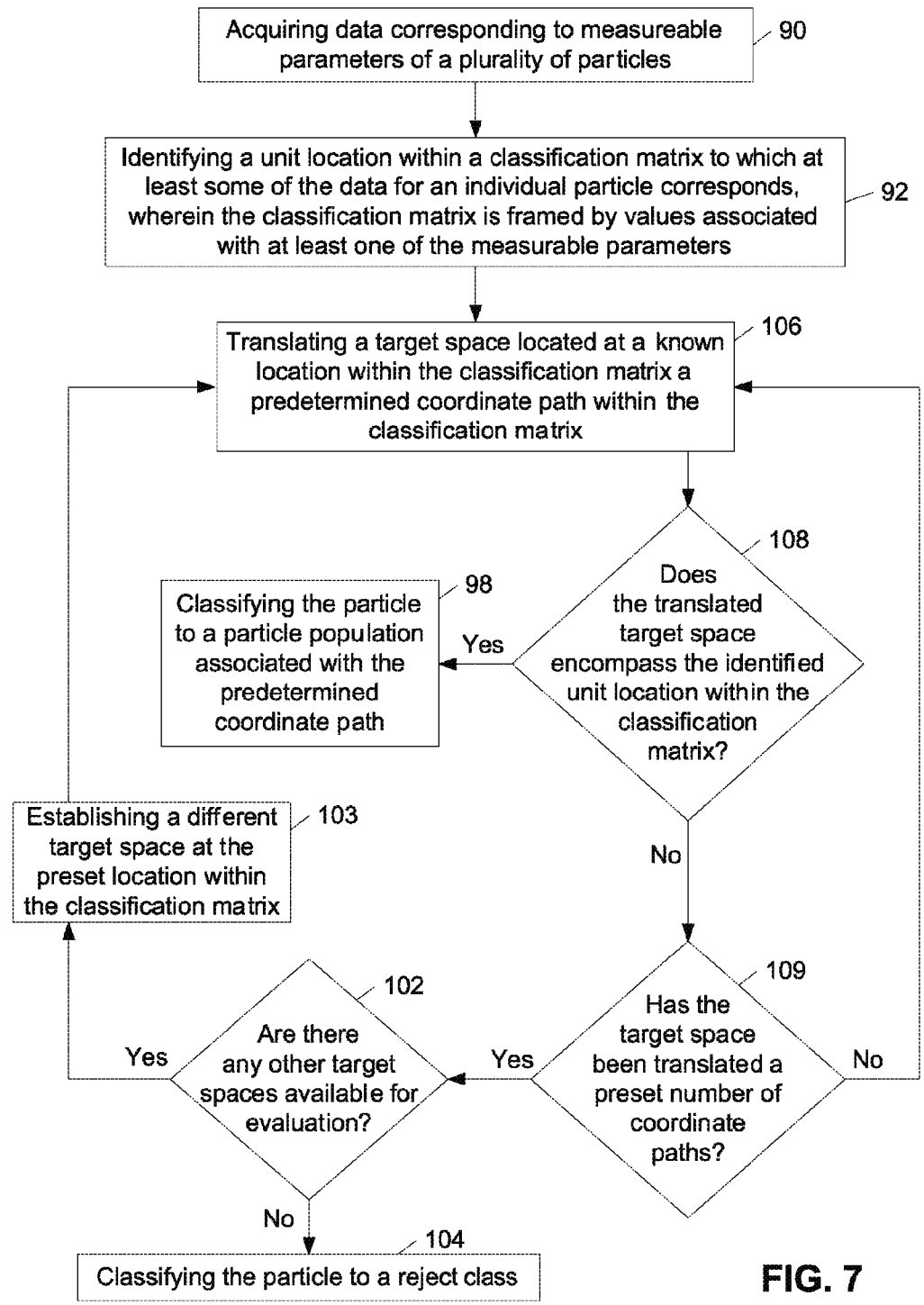

FIG. 7 illustrates a flowchart of an alternative process for classifying a particle. The process is similar to the process depicted in FIG. 6 in that it includes process steps discussed in reference to blocks 90, 92, 98, 102, 103, and 104. The specifics of such process steps discussed above with respect to FIG. 6 may be applied to the corresponding process steps depicted in FIG. 7 and are not reiterated for the sake of brevity. The process for classifying particles in FIG. 7 differs from the method outlined in FIG. 6 by inclusion of blocks 106, 108, and 109 (i.e., replacing blocks 94, 96, and 98 in FIG. 6). In particular, instead of translating the data corresponding to the unit location identified in block 92 to attempt to fit into a target space at a known location, blocks 106, 108, and 109 in FIG. 7 are directed to translating a target space to attempt to encompass the identified unit location corresponding to acquired data for a particle.

More specifically, block 106 includes translating a target space located at a known location within the classification matrix a predetermined coordinate path and block 108 determines whether the translated target space encompasses the identified unit location of the classification matrix corresponding to acquired data for a particle. The predetermined coordinate path may be characterized in a similar manner as described in reference to FIG. 6 and, thus, is not reiterated for the sake of brevity. It is noted that in embodiments in which block 92 comprises identifying a segment of the classification matrix which includes the identified unit location, block 106 may comprise translating the target space a predetermined coordinate path which is associated with the identified segment. Identifying a corresponding segment of the classification matrix and translating the target space a predetermined coordinate path associated with the identified segment, however, is optional. To illustrate the translation of target space, FIG. 9 depicts an exemplary graphical representation of a target space within a classification matrix translated a predetermined coordinate path to an identified unit location (i.e., the target space is denoted as the cross-hatched elliptical region, the coordinate path is denoted by the dotted line, and the identified unit location is denoted by the asterisk).

As shown in FIG. 7, upon determining the translated target space encompasses the identified unit location at block 108, the method proceeds to block 98 to classify the particle to a particle population associated with the predetermined coordinate path. On the contrary, if it is determined that the translated target space does not encompass the identified unit location at block 108, the process continues to block 109 at which a determination is made whether the target space has been translated a preset number of different coordinate paths. The preset number of coordinate paths may vary among systems and assay applications. The sequence of process steps subsequent to block 109 is similar to the sequence of process steps outlined in FIG. 6 subsequent to block 100 and, thus, is not reiterated for the sake of brevity.

As denoted in block 106 of FIG. 7, the target space is located at a known location within the classification matrix. The known location may be any location within the classification matrix. In some embodiments, the target space may include the origin of the axes framing the classification matrix and in specific cases the target space may be centered at the origin. In general, the target space may be of any configuration (i.e., size, shape, etc.). As with the method described in reference to FIG. 6, the target space may be representative of a single classification region configuration or multiple classification region configurations stacked upon each other. In other words, the target space may include a periphery of a single classification region configuration or a periphery of multiple classification region configurations centered about the same point. Exemplary processes for determining if and which of such multiple classification regions a target space may be translated to are outlined and described in more detail below with respect to FIGS. 11 and 12.

It is noted that the differences between the methods described in reference to FIGS. 6 and 7 offer different advantages and, therefore, the determination of which method to use may depend on the application. For example, the method described in reference to FIG. 6 offers an advantage of employing comparatively fewer computations to translate the data associated with the identified unit location versus translating an entire target shape. This is because translating involves an addition or subtraction operation for each unit location of an item being translated. Target spaces are typically composed of tens, hundreds, or even thousands of unit locations and, thus, translating a target space involves a lot more computations that translating data associated with a single unit location as taught in reference to FIG. 6. Consequently, the method presented in FIG. 6 involves fewer computations and, thus, may offer significantly faster processing times than the method presented in FIG. 7 in some embodiments. In some cases, however, the method presented in FIG. 7 may offer faster processing times than the method presented in FIG. 6, since the method presented in FIG. 7 may involve translating a target space fewer times than translating data corresponding to a single unit location. In particular, since a target space generally spans tens, hundreds, or even thousands of unit locations, the number of coordinate paths it may take to cover a classification matrix to determine if the target space encompasses a particular unit location will take fewer iterations than trying to translate data associated with a single unit location across a classification matrix.

Figure 11:
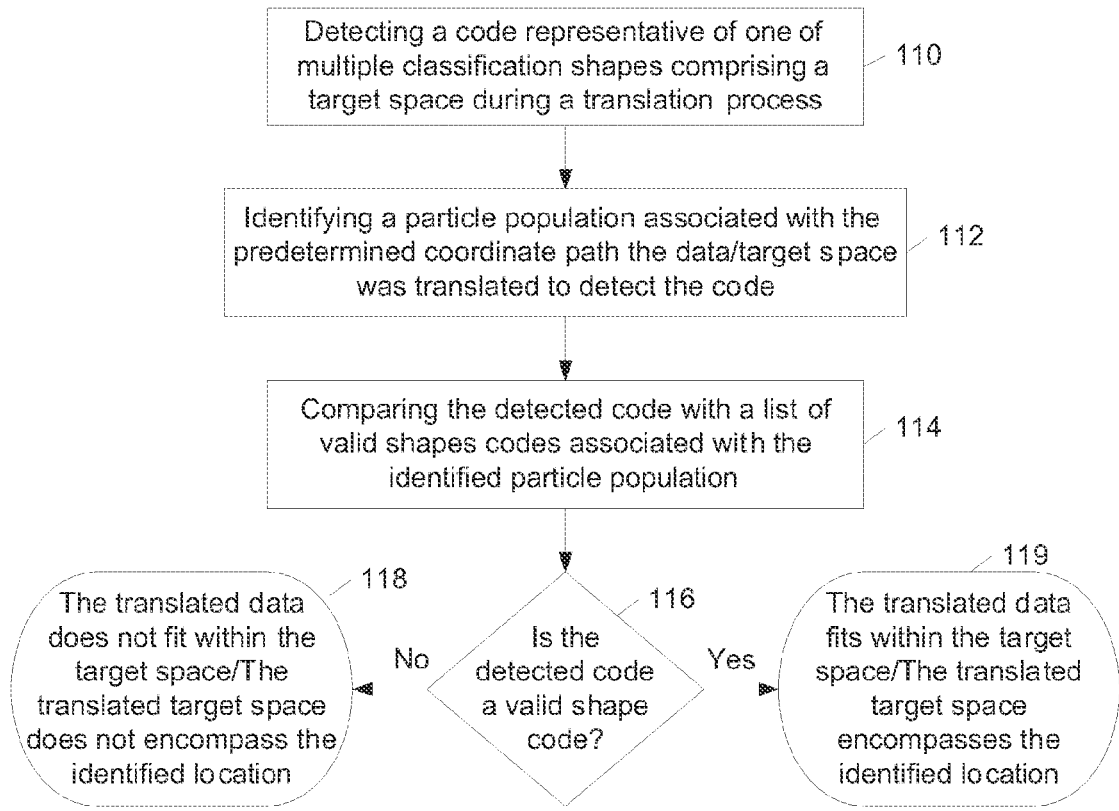
FIGS. 11 and 12 illustrate flowcharts for exemplary techniques for determining if and which of a plurality of classification region configurations a data point or a target space may be translated to when a target space representing a plurality of classification region configurations is used in either of the methods described in reference to FIGS. 6 and 7.
Figure 12:
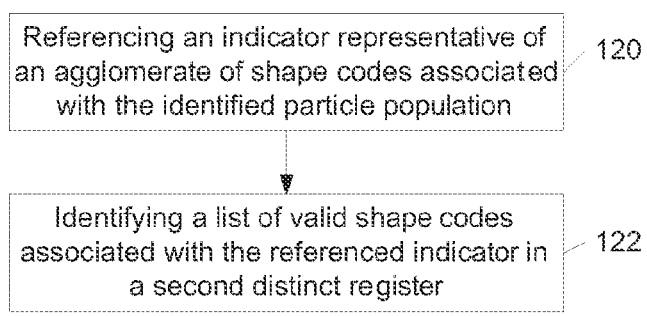

As noted above, FIGS. 11 and 12 illustrate flowcharts for exemplary techniques for determining if and which of a plurality of classification region configurations information may be translated to when a target space representing the plurality of classification region configurations is used in either of the methods described in reference to FIGS. 6 and 7. In particular, FIGS. 11 and 12 illustrate flowcharts of exemplary methods for determining whether translated information fits within a target space or encompasses an identified unit location of a classification matrix (i.e., relating to blocks 96 and 108 of FIGS. 6 and 7, respectively). And, if so, the methods outlined in FIGS. 11 and 12 further determine which of a plurality classification region configurations associated with the target space corresponds to the predetermined coordinate path used for the translation. FIG. 10 illustrates an exemplary target space representing 4 distinct classification shapes. FIG. 10 is discussed in conjunction with the processes described in reference to FIGS. 11 and 12. The distinct configuration shapes illustrated in FIG. 10 are respectively referenced as shapes 1-4. Shape 1 is a relatively small circular design, while shape 2 is a relatively larger circular ring encompassing shape 1. Shapes 3 and 4 each include appendages extending from the circular body of shape 2. As used herein, the term "classification shape" generally refers to a distinct area of a target space having a configuration that is representative of at least a portion of one or more classification region configurations for a classification matrix.

As shown in FIG. 11, the process outlined therein may include block 110 in which a code representative of one of a multiple classification shapes comprising a target space is detected during a translation process. More specifically, a code representative of one of a multiple of classification shapes of a target space may be detected when data corresponding to an identified unit location is translated a predetermined coordinate path and resultantly fits within the target space. Alternatively, a code representative of one of a multiple of classification shapes of a target space may be detected when the target space is translated a predetermined coordinate path and resultantly encompasses an identified unit location. For example, any one of codes 1-4 may be detected when the exemplary target space illustrated in FIG. 10 is used for either case. The method further includes, as denoted in block 112, identifying a particle population associated with the predetermined coordinate path the data or target space was translated to detect the code. Such an identification process may generally involve referencing a database or look-up table which is accessible and, in some cases, stored by the storage medium and/or system performing the process. An exemplary look-up table for the identification of a particle population is shown below in Table 3, but such a table is merely exemplary and should not be construed to limit the scope of the identification process. For example, the coordinate paths are not restricted to three dimensions nor are the number of particle populations limited to 500.

TABLE 3

Exemplary Look-Up Table for Identifying Particle Populations Based on Translation Coordinate Paths

| Coordinate Path | Particle Population |
|---|---|
| (1, 0, 0) | 1 |
| (1, 1, 0) | 2 |
| ... | ... |
| (X, X, X) | 500 |

Subsequent to identifying the particle population associated with the coordinate path used to translate the information in the classification matrix in block 112, the method continues to block 114 to compare the code detected in the process outlined in block 110 with a list of valid shape codes associated with the identified particle population. Thereafter, the method includes determining whether the detected code is valid as denoted in block 116. As with block 112, such a comparison process may generally involve referencing a database or look-up table which is accessible and, in some cases, stored by the storage medium and/or system performing the process. In particular, the process of comparing the detected code with a list of valid shape codes (i.e., block 114 of FIG. 11) may, in some embodiments, include identifying a list of valid shape codes in a register listing of valid shape codes for each particle population included within an assay.

An exemplary look-up table for validating detected codes using such a technique is shown below in Table 4, but such a table is merely exemplary and should not be construed to limit the scope of the validation process. For example, the number of particles populations and the number of valid classification shapes associated with the particle populations are not restricted to the numbers denoted in the table.

TABLE 4

Exemplary Look-Up Table for Validating Codes Associated with Identified Particle Populations

| Particle Population | Valid Shape Codes |
|---|---|
| 1 | 1, 2, 3 |
| 2 | 2, 3 |
| ... | ... |
| 500 | 1, 2, 3, 4 |

Using Tables 3 and 4 and the target space depicted in FIG. 10 in relation to the processes outlined in blocks 110-116 of FIG. 11, several different scenarios may be delineated to explain the process of validating a classification process utilizing shapes of a target space which is representative of a plurality of classification region configurations. For example, in an embodiment in which a code of "2" is detected for the process outlined in 110 in relation to the target space depicted in FIG. 10 and a coordinate path used in the translation process is (1, 1, 0), then according to Table 3 the particle population associated with the coordinate path is 2 and according to Table 4 the detected code is valid for such a particle population. In contrast, in an embodiment in which a code of "1" is detected for the process outlined in 110 in relation to the target space depicted in FIG. 10 and a coordinate path used in the translation process is (1, 1, 0), then according to Table 3 the particle population associated with the coordinate path is 2 and according to Table 4 the detected code is not valid for such a particle population.

An alternative process for comparing the code detected in the process outlined in block 110 with a list of valid shape codes (i.e., block 114 in FIG. 11) may include the process steps outlined in the flowchart depicted in FIG. 12. In particular, the process of comparing the detected code with a list of valid shape codes in block 114 of FIG. 11 may include first referencing an indicator representative of an agglomerate of shape codes associated with the identified particle population in a first register as noted in block 120 of FIG. 12. In addition, the process may include identifying a list of valid shape codes associated with the referenced indicator in a second distinct register as noted in block 122 of FIG. 12. As with descriptions noted above, such referencing and identifying processes may generally involve referencing a database or look-up table which is accessible and, in some cases, stored by the storage medium and/or system performing the process. Exemplary look-up tables for referencing an indicator of configuration codes and identifying a corresponding list of valid classification codes are shown below in Tables 5 and 6, respectively, but such tables are exemplary and should not be construed to limit the scope of the processes. For example, the number of particles populations, the number of shape code indicators, and the number of valid shape codes are not restricted to the numbers denoted in the tables.

TABLE 5

Exemplary Look-Up Table for Referencing Configuration Indicators Associated with Identified Particle Populations

| Particle Population | Configuration Indicator |
|---|---|
| 1 | A |
| 2 | B |
| 3 | A |
| 4 | C |
| ... | ... |
| 500 | B |

TABLE 6

Exemplary Look-Up Table for Validating Codes Associated with Identified Configuration Indicators

| Configuration Indicator | Valid Shape Codes |
|---|---|
| A | 1, 2, 3 |
| B | 1, 2 |
| C | 1, 2, 4 |

Using Tables 5 and 6 in relation to the processes outlined in blocks 120 and 122 of FIG. 12, several different scenarios may be delineated to determine whether a code detected in the process outlined in block 110 of FIG. 11 is valid. For example, in an embodiment in which a code of "2" is detected for the process outlined in 110 in FIG. 11 and the particle population identified for the process outlined in 112 of FIG. 11 is 2, then according to Table 5 a configuration indicator of "B" is referenced for particle population "2" and according to Table 6 the detected code is valid for such a configuration indicator. In contrast, in an embodiment in which a code of "4" is detected for the process outlined in 110 in FIG. 11 and the particle population identified for the process outlined in 112 of FIG. 11 is 2, then according to Table 5 a configuration indicator of "B" is referenced for particle population "2" and according to Table 6 the detected code is not valid for such a configuration indicator.

The benefit the process steps outlined in FIG. 12 offer is the potential for significantly reducing memory needs, particularly when a lot of classification region configurations (e.g., greater than 5 classification region configurations) are included within a target space. More specifically, the memory usage of a system significantly increases when one or more of several valid shape codes need to be stored for each particle population. The process steps and accompanying databases referred to in FIG. 12, however, allows fewer codes to be stored for each particle population and, thus, less memory is needed to perform such functions.

Regardless of the processes utilized for block 114 in FIG. 11, the method continues to block 116 to determine whether the detected code is valid for the identified particle population. Upon determining the detected code is valid for the identified particle population, the method continues to block 119 to declare the translated data fits within the target space or the translated target space encompasses the identified unit location, depending which method is employed with respect to FIGS. 6 and 7. In contrast, upon determining the detected code is invalid for the identified particle population, the method routes to block 118 at which it is declared that the translated data does not fit within the target space or the translated target space does not encompass the identified unit location, depending which method is employed with respect to FIGS. 6 and 7.

To aid delineating some of the terms used herein, the following definitions are provided:

Particle Population—a set of particles having similar properties

Particle Population Category—a grouping of possible measured values for one or more parameters of a particle population Classification matrix—an array of values (actual or virtual) corresponding to measured parameters of particles used for classification Classification region—an area of a classification matrix to which a population of particles may be classified Classification Region Configuration—a set design of a classification region as characterized by its shape, size, etc.

Target Space—a bounded area having a periphery which is indicative of one or more classification region configurations stacked upon each other Unit Location—a specific coordinate point within a classification matrix Classification shape—a distinct area of a target space having a configuration that is representative of at least a portion of one or more classification region configurations for a classification matrix It will be appreciated to those skilled in the art having the benefit of this disclosure that this invention is believed to provide methods, storage mediums, and systems for configuring classification regions within a classification matrix of an assay analysis system as well as methods, storage mediums, and systems for classifying particles of an assay. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A non-transitory storage medium comprising program instructions which are executable by a processor for:
   identifying a plurality of classification regions within a classification matrix which is framed by ranges of values associated with one or more measurable parameters of particles that are configured for assay analysis;
   reassigning unit locations jointly assigned to two or more of the plurality of classification regions as non-classification regions;
   computing a quantity of the jointly assigned unit locations within the classification matrix prior to reassigning unit locations of the classification matrix as non-classification regions;
   adjusting values of one or more dimensional attributes of one or more of the plurality of classification regions upon computing a quantity of jointly assigned unit locations above a predetermined threshold;
   identifying unit locations within the classification matrix jointly assigned to two or more of the classification regions subsequent to adjusting values of one or more dimensional attributes of one or more of the classification regions; and iterating the steps of computing a quantity of the jointly assigned unit locations within the classification matrix, adjusting values of one or more dimensional attributes of one or more of the plurality of classification regions, and identifying unit locations within the classification matrix jointly assigned to two or more of the classification regions until a quantity of jointly assigned unit locations within the classification matrix is computed to be equal to or below the predetermined threshold, wherein the program instructions for reassigning unit locations of the classification matrix as non-classification regions comprise program instructions for reassigning the jointly assigned unit locations associated with the classification regions having the quantity of jointly assigned unit locations computed to be equal to or below the predetermined threshold as non-classification regions.

2. The non-transitory storage medium of claim 1, wherein the program instructions are further executable by the processor for further reassigning unit locations adjacent to the jointly assigned unit locations as non-classification regions.

3. The non-transitory storage medium of claim 1, wherein the program instructions are further executable by the processor for:

computing a quantity of the jointly assigned unit locations within the classification matrix prior to reassigning unit locations of the classification matrix as non-classification regions;

adjusting values of one or more dimensional attributes of one or more of the plurality of classification regions;

identifying unit locations within the classification matrix jointly assigned to two or more of the classification regions subsequent to adjusting values of one or more dimensional attributes of one or more of the classification regions; and iterating the steps of computing a quantity of the jointly assigned unit locations within the classification matrix, adjusting values of one or more dimensional attributes of one or more of the plurality of classification regions, and identifying unit locations within the classification matrix jointly assigned to two or more of the classification regions a predetermined number of times, wherein the program instructions for reassigning unit locations of the classification matrix as nonclassification regions comprise program instructions for reassigning the jointly assigned unit locations associated with the classification regions having the smallest quantity of jointly assigned unit locations as non-classification regions.

4. The non-transitory storage medium of claim 1, wherein the plurality of classification regions are ellipsoidal, and wherein the program instructions for adjusting values of the one or more dimensional attributes comprises adjusting values of at least one of a major axis, a minor axis, an elevation angle, and an azimuth angle of one or more of the plurality of classification regions.

5. The non-transitory storage medium of claim 1, wherein the program instructions are further executable by the processor for:

acquiring data corresponding to measurable parameters of a plurality of particles;
identifying unit locations within the classification matrix to which at least some of the data corresponds;

calculating a classification efficiency of the plurality of particles relative to the plurality of classification regions;

adjusting values of one or more dimensional attributes of one or more of the plurality of classification regions upon calculating a classification efficiency below a predetermined threshold; and repeating the steps of calculating a classification efficiency and adjusting values of one or more dimensional attributes upon calculating a classification efficiency below a predetermined threshold until a classification efficiency equal to or above the predetermined threshold is calculated.

6. The non-transitory storage medium of claim 5, wherein the program instructions are further executable by the processor for repeating the steps of calculating a classification efficiency and adjusting values of the one or more dimensional attributes prior to the step of reassigning unit locations of the classification matrix as non-classification regions.

7. The non-transitory storage medium of claim 5, wherein the program instructions are further executable by the processor for repeating the steps of calculating a classification efficiency and adjusting values of the one or more dimensional attributes subsequent to the step of reassigning unit locations of the classification matrix as non-classification regions.

8. A system comprising:
a processor; and
storage medium comprising program instructions which are executable by the processor for:
mathematically transforming a first value that corresponds to a point within an assay particle population category into a second value;
converting the second value to a first integer;
mathematically transforming the first integer into a third value by applying a transformation formula to the first integer which is inverse to the transformation formula used to mathematically transform the first value;
converting the third value to a second integer;
designating the second integer as a replacement value for the point within the assay particle population category;
mathematically transforming the second integer into a fourth value by applying to the second integer the transformation formula used to mathematically transform the first value;
calculating a first difference between the fourth value and its nearest integer;
calculating a second difference between the second value and its nearest integer; and
revoking the designation of the second integer as the replacement value upon determining the second difference is less than the first difference.

9. The system of claim 8, wherein the program instructions for mathematically transforming the first value that corresponds to the point within the assay particle population category comprise program instructions for mathematically transforming a value that corresponds to a point central to the assay particle population category.

10. The system of claim 8, further comprising program instructions for designating the second integer as a target for dyeing a particle population for assay analysis.

11. The system of claim 8, wherein the program instructions for mathematically transforming the first value comprises program instructions for mathematically processing the first value in a logarithmic based formula, a formula comprising an exponential, a formula comprising a power, a formula comprising a binomial, a formula comprising a Taylor or MacLaurin series, a formula comprising a parametric equation, a formula comprising a coordinate transformation, or a formula in which the first value is multiplied by or added to a constant.

12. The system of claim 8, further comprising program instructions for:
    mathematically transforming the second integer into a fourth value by applying to the second integer the transformation formula used to mathematically transform the first value;
    calculating a difference between the fourth value and its nearest integer; and
    revoking the designation of the second integer as the replacement value upon calculating a difference greater than a predetermined threshold.

13. The system of claim 8, wherein the program instructions are further executable by the processor for:
    repeating, for each of a plurality of different assay particle population categories, the steps of mathematically transforming a first value that corresponds to a point within a respective assay particle population category into a second value, converting the second value to a first integer, mathematically transforming the first integer into a third value by applying a formula to the first integer which is inverse to the transformation formula used to mathematically transform the first value, converting the third value to a second integer, and designating the second integer as a replacement value corresponding to the point within the respective assay particle population category;
    mathematically transforming each the second integers calculated for each of the plurality of different assay particle population categories into fourth values by applying to the second integers the transformation formula used to mathematically transform the first values corresponding to the points in each of the plurality of different assay particle population categories;
    calculating differences between the fourth values and their respectively nearest integers;
    calculating a percentage of the differences that are above a predetermined threshold; and
    revoking the designation of the second integers as the replacement values upon calculating a percentage greater than a preset level.

14. A method executed by a computer, comprising:
    acquiring data, with the computer, corresponding to measurable parameters of a particle;
    identifying a unit location within a classification matrix to which at least some of the data for an individual particle corresponds, wherein the classification matrix is framed by values associated with at least one of the measurable parameters;
    translating in the computer the data corresponding to the identified unit location a predetermined coordinate path within the classification matrix;
    determining whether the translated data fits within a target space located at a preset location within the classification matrix;
    repeating the steps of translating the data and determining whether the translated data fits within the target space for different predetermined coordinate paths within the classification matrix until one of two conclusive actions is conducted, wherein the two conclusive actions comprise:
        determining the translated data fits within the target space; and
        translating the data a preset number of predetermined coordinate paths without determining the translated data fits within the target space;
    upon determining the translated data fits within the target space, classifying the particle to a particle population associated with the predetermined coordinate path the data was translated to fit into the target space; and
    upon translating the data the preset number of predetermined coordinate paths without determining the translated data fits within the target space, performing one of two action items, wherein the action items comprise:
        classifying the particle to a reject class if no other target spaces are available for evaluation; and
        repeating the steps of translating the data and determining whether the translated data fits within a different target space via the predetermined coordinate paths until one of the two conclusive actions is conducted.

15. The method executed by a computer of claim 14, wherein the step of identifying a unit location within a classification matrix further comprises identifying a segment of the classification matrix comprising the unit location, and wherein the step of translating the data comprises translating the data a predetermined coordinate path which is associated with the identified segment.

16. The method executed by a computer of claim 14, wherein at least one of the target space and the different target space comprises a periphery of a single classification region configuration.

17. The method of executed by a computer claim 14, wherein at least one of the target space and the different target space comprises a periphery of multiple classification region configurations centered about the same point.

18. The method executed by a computer of claim 17, wherein the step of determining whether the translated data fits within the target space comprises:
    detecting a code representative of one of a multiple of classification shapes comprising the target space during the step of translating the data;
    identifying a particle population associated with the predetermined coordinate path the data was translated to detect the code;
    comparing the detected code with a list of valid shape codes associated with the identified particle population;
    determining the translated data fits within the target space upon determining the detected code is listed as a valid shape code for the identified particle population; and
    determining the translated data does not fit within the target space upon determining the detected code is not listed as a valid shape code for the identified particle population.

19. The method executed by a computer of claim 18, wherein the step of comparing the detected code with a list of valid shape codes comprises identifying the list of valid shape codes in a register listing valid shape codes for each particle population included in the classification matrix.

20. The method executed by a computer of claim 18, wherein the step of comparing the detected code with a list of valid shape codes comprises:
    referencing an indicator representative of an agglomerate of shape codes associated with the identified particle population in a first register; and
    identifying a list of valid shape codes associated with the referenced indicator in a second distinct register.

21. A non-transitory storage medium comprising program instructions which are executable by a processor for:
    acquiring data corresponding to measurable parameters of a particle;

identifying a unit location within a classification matrix to which at least some of the data for an individual particle corresponds, wherein the classification matrix is framed by values associated with at least one of the measurable parameters;

translating a target space located at a known location within the classification matrix a predetermined coordinate path within the classification matrix;

determining whether the translated target space encompasses the identified unit location of the classification matrix;

reiterating the steps of translating the target space and determining whether the translated target space encompasses the identified unit location for different predetermined coordinate paths within the classification matrix until one of two conclusive actions is conducted, wherein the two conclusive actions comprise:

determining the translated target space encompasses the identified unit location; and translating the target space a preset number of predetermined coordinate paths without determining the target space encompasses the identified unit location;

upon determining the translated target space encompasses the identified unit location, classifying the particle to a particle population associated with the predetermined coordinate path the target space was translated to encompass the identified unit location; and upon translating the target space the preset number of predetermined coordinate paths without determining the target space encompasses the identified unit location, performing one of two action items, wherein the action items comprise:

classifying the particle to a reject class if no other target spaces are available for evaluation; and repeating the steps of translating a different target space and determining whether the different translated target space encompasses the identified unit location via the predetermined coordinate paths until one of the two conclusive actions is conducted.

22. The non-transitory storage medium of claim 21, wherein program instructions for identifying a unit location within a classification matrix further comprise program instructions for identifying a segment of the classification matrix comprising the unit location, and wherein the program instructions for translating the target space comprise program instructions for translating the target space a predetermined coordinate path which is associated with the identified segment.

23. The non-transitory storage medium of claim 21, wherein at least one of the target space and the different target space comprises a periphery of a single classification region configuration.

24. The non-transitory storage medium of claim 21, wherein at least one of the target space and the different target space comprises a periphery of multiple classification region configurations centered about the same point.

25. The non-transitory storage medium of claim 24, wherein the program instructions for determining whether the translated target space encompasses the identified unit location comprise program instructions for:

detecting a code representative of one of a multiple of classification shapes comprising the target space during the step of translating the target space;

identifying a particle population associated with the predetermined coordinate path the target space was translated to detect the code;

comparing the detected code with a list of valid shape codes associated with the identified particle population;

determining the translated target space encompasses the identified unit location upon determining the detected code is listed as a valid shape code for the identified particle population; and determining the translated target space does not encompass the identified unit location upon determining the detected code is not listed as a valid shape code for the identified particle population.

26. The non-transitory storage medium of claim 25, wherein the program instructions for comparing the detected code with a list of valid shape codes comprise program instructions for identifying the list of valid shape codes in a register listing valid shape codes for each particle population included in the classification matrix.

27. The non-transitory storage medium of claim 25, wherein the program instructions comparing the detected code with a list of valid classification codes comprise program instructions for:

referencing an indicator representative of an agglomerate of shape codes associated with the identified particle population in a first register; and identifying a list of valid shape codes associated with the referenced indicator in a second distinct register.

* * * * *